(12) United States Patent
Vink

(10) Patent No.: US 11,795,474 B2
(45) Date of Patent: Oct. 24, 2023

(54) STABLE CELL LINES FOR RETROVIRAL PRODUCTION

(71) Applicant: GlaxoSmithKline Intellectual Property Development Limited, Brentford (GB)

(72) Inventor: Conrad Vink, Stevenage (GB)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 150 days.

(21) Appl. No.: 16/606,281

(22) PCT Filed: Apr. 18, 2018

(86) PCT No.: PCT/EP2018/059917
§ 371 (c)(1),
(2) Date: Oct. 18, 2019

(87) PCT Pub. No.: WO2018/192981
PCT Pub. Date: Oct. 25, 2018

(65) Prior Publication Data
US 2020/0095606 A1    Mar. 26, 2020

(30) Foreign Application Priority Data
Apr. 18, 2017 (GB) .................................. 1706121

(51) Int. Cl.
C12N 15/00 (2006.01)
C12N 15/86 (2006.01)
C07K 14/16 (2006.01)

(52) U.S. Cl.
CPC ............ *C12N 15/86* (2013.01); *C07K 14/161* (2013.01); *C07K 14/162* (2013.01);
(Continued)

(58) Field of Classification Search
None
See application file for complete search history.

(56) References Cited

U.S. PATENT DOCUMENTS 5,278,056 A    1/1994 Bank et al.
6,677,155 B1 *  1/2004 Sena-Esteves ....... C07K 14/005
                                                   424/93.21
(Continued)

FOREIGN PATENT DOCUMENTS

GB    2538321 A    11/2016
GB    2538324 A    11/2016
(Continued)

OTHER PUBLICATIONS

Ni et al., "Generation of a packaging cell line for prolonged large-scale production of high-titer HIV-1-based lentiviral vector," The Journal of Gene Medicine 7: 818-834 (Year: 2005).*
(Continued)

*Primary Examiner* — M Franco G Salvoza
(74) *Attorney, Agent, or Firm* — Carly Shanahan

(57) ABSTRACT

The invention relates to retroviral producer cell comprising nucleic acid sequences encoding: gag and pol proteins; envelope protein or a functional substitute thereof; amplifiable selection marker; and the RNA genome of the retroviral vector particle, wherein said nucleic acid sequences are all integrated at a single locus within the retroviral producer cell genome. The invention also relates to nucleic acid vectors comprising a non-mammalian origin of replication and the ability to hold at least 25 kilobases (kb) of DNA, characterized in that said nucleic acid vector comprises retroviral nucleic acid sequences encoding: gag and pol proteins, and an env protein or a functional substitute thereof. The nucleic acid vector additionally comprises nucleic acid sequences encoding an amplifiable selection marker. The invention
(Continued)

Figure 1:
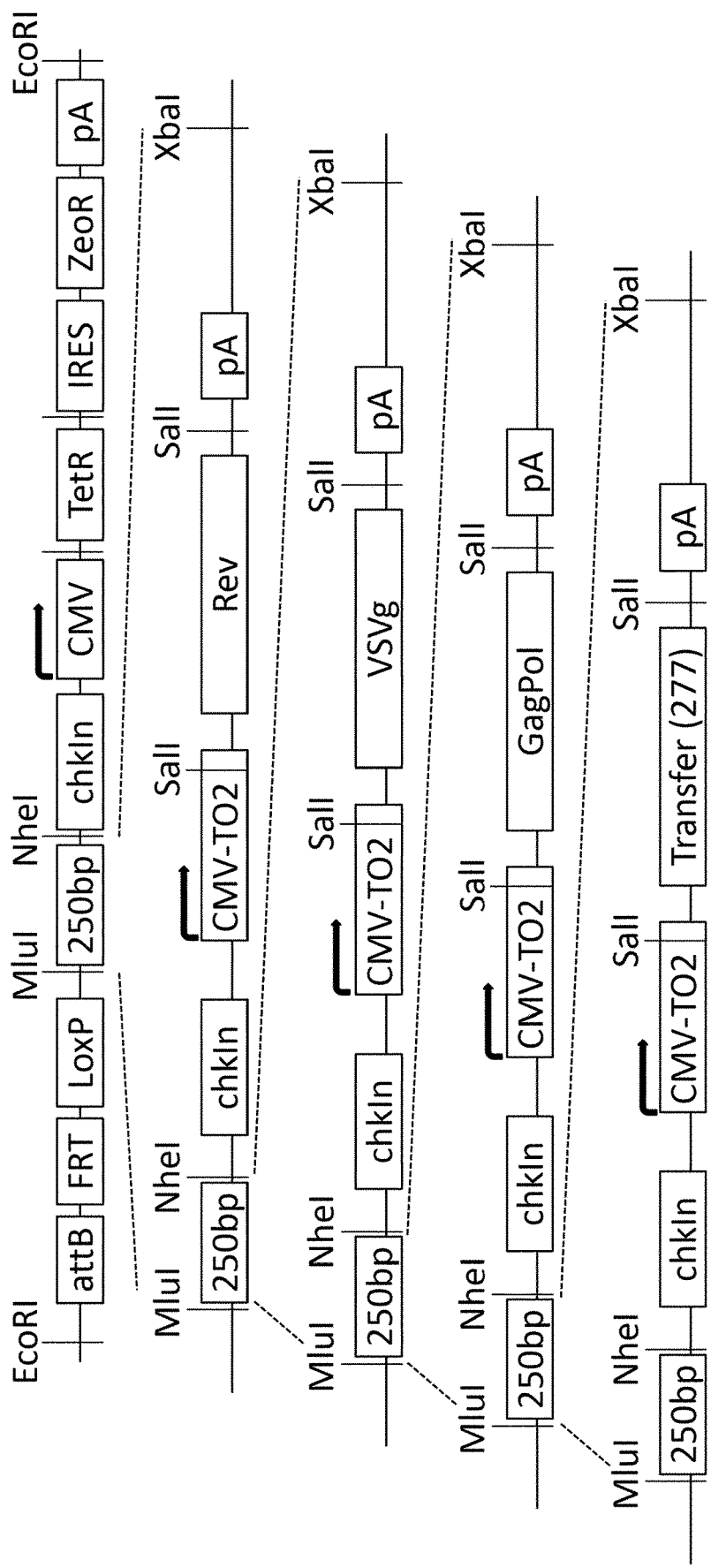

also relates to uses and methods using said nucleic acid vector in order to produce stable retroviral packaging and producer cell lines.

29 Claims, 13 Drawing Sheets

Specification includes a Sequence Listing.

(52) U.S. Cl.
CPC .............. *C12N 2740/13052* (2013.01); *C12N 2740/15052* (2013.01); *C12N 2740/16052* (2013.01); *C12N 2799/027* (2013.01); *C12N 2830/003* (2013.01); *C12N 2830/006* (2013.01); *C12N 2830/60* (2013.01)

(56) References Cited

U.S. PATENT DOCUMENTS

| | | | |
|---|---|---|---|
| 2001/0036655 A1 | 11/2001 | Pavlakis | |
| 2003/0138954 A1* | 7/2003 | Trono | C07K 14/70503 435/456 |
| 2011/0312029 A1* | 12/2011 | Enenkel | C12N 15/63 435/69.1 |
| 2020/0095606 A1 | 3/2020 | Vink | |

FOREIGN PATENT DOCUMENTS

| | | | |
|---|---|---|---|
| JP | 2005-503778 | 2/2005 | |
| JP | 2005-523688 | 8/2005 | |
| WO | 02/097059 | 12/2002 | |
| WO | 03/062395 | 7/2003 | |
| WO | WO-2008099148 A1 * | 8/2008 | ........... C07K 14/005 |
| WO | 2010148203 A2 | 12/2010 | |
| WO | WO 2012/028681 A1 | 3/2012 | |
| WO | 2015112541 A2 | 7/2015 | |
| WO | WO 2017/089307 A1 | 6/2017 | |
| WO | WO 2017/089308 A1 | 6/2017 | |

OTHER PUBLICATIONS

Qian Brian, et al., *Nucleic Acids Research*, BAC TG—EMBED : one-step method for high-level,copy-number-dependent,position-independent transgene expression, 38(11):e127 (2010).

Noriko Suzuki ,et al., *Molecular Therapy*, 937. A Novel Transfection-Free Packaging Strategy of HIV Vectors Using a CHO Based Packaging Cell Line and an Adenovirus Based Expression Vectors, 5(5):S306 (2002).

* cited by examiner

GFP fluorescent images of stable cell lines
Clone 1
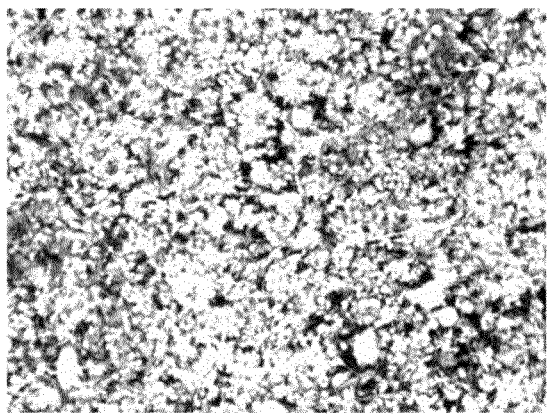
Clone 14
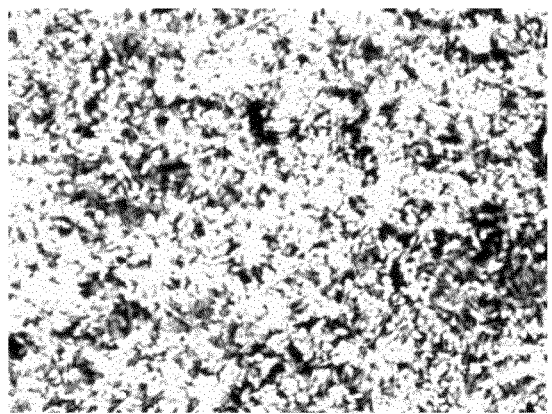
Clone 15
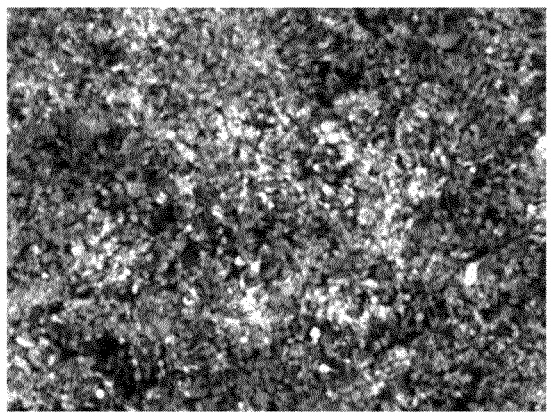
Clone 16
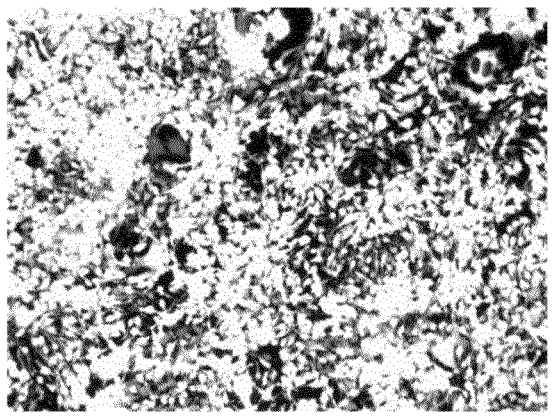
FIGURE 3

```
5401                       cagctgtgg aatgtgtgtc agtagggtg tggaaagtcc ccaggctccc
5461 cagcaggcag aagtatgcaa agcatgcatc tcaattagtc agcaaccagg tgtggaaagt
5521 cccaggctc cccagcaggc agaagtatgc aaagcatgca tctcaattag tcagcaacca
5581 tagtcccgcc cctaactccg cccatcccgc cctaactcc gccagttcc gccattctc
5641 cgccccatgg ctgactaatt tttttattt atgcagaggc cgaggccgcc tcgcctctg
5701 agctattcca gaagtagtga ggaggctttt ttggaggcct aggctttgc aaaagcttt
5761 cttggatagc ttgggggggg gacagctcag ggctgcgatt tcgcgccaaa cttgacggca
5821 atcctagcgt gaaggctggt aggatttat cccgctgcc atcatggttc gaccattgaa
5881 ctgcatcgtc gccgtgtccc aagatatggg gattggcaag aacggagacc tacctgcc
5941 tccgctcagg aacgagttca agtacttcca aagaatgacc acaacctct cagtggaagg
6001 taaacagaat ctggtgatta tgggtaggaa aacctggttc tccattcctg agaagaatcg
6061 acctttaaag gacagaatta atatagttct cagtagagaa ctcaaagaac caccacgagg
6121 agctcatttt cttgccaaaa gttggatga tgccttaaga cttattgaac aacggaatt
6181 ggcaagtaaa gtagacatgg tttggatagt cggaggcagt tctgtttacc aggaagccat
6241 gaatcaacca ggccaccta gactctttgt gacaaggatc atgcaggaat ttgaaagtga
6301 cacgttttc ccagaaattg atttgggaa atataaactt ctcccagaat accaggcgt
```

FIGURE 7

```
6361 cctctctgag gtccaggagg aaaaaggcat caagtataag tttgaagtct acgagaagaa
6421 agactaagat ctttgtgaag gaaccttact tctgtggtgt gacataattg gacaaactac
6481 ctacagagat ttaaagctct aagtaaata taaaattttt aagtgtataa tgtgttaaac
6541 tactgattct aattgttgt gtattttaga ttccaaccta tggaactgat gaatgggagc
6601 agtggtggaa tgcctttaat gaggaaaacc tgttttgctc agaagaaatg ccattcagtg
6661 atgatgaggc tactgctgac tctcaacatt ctactcctcc aaaaaagaag agaaaggtag
6721 aagacccca ggactttcct tcagaattgc taagttttt gagtcatgct gtgtttagta
6781 atagaactct tgcttgcttt gctatttaca ccacaaagga aaaagctgca ctgctataca
6841 agaaaattat ggaaaaatat tctgtaacct ttataagtag gcataacagt tataatcata
6901 acatactgtt ttttcttact ccacacaggc atagagtgtc tgctattaat aactatgctc
6961 aaaaattgtg tacctttagc tttttaattt gtaaaggggt taataaggaa tatttgatgt
7021 atagtgcctt gactagagat cataatcagc cataccacat ttgtagaggt tttacttgct
7081 ttaaaaacc tcccacacct cccctgaac ctgaaacata aatgaatgc aattgttgtt
7141 gttaacttgt ttattgcagc ttataatggt tacaaataaa gcaatagcat cacaaatttc
7201 acaaataaag cattttttc actgcattct agtgtgtggt tgtccaaact catcaatgta
```

FIGURE 7 (continued)

7261 tcttatcatg tctggatccc caggaagctc ctctgtgtcc tcataaaccc taacctcctc
7321 tacttgagag gacattccaa tcataggctg cccatccacc ctctgtgtcc tcctgttaat
7381 taggtcactt aacaaaaagg aaattgggta ggggtttttc acagaccgct ttctaaggt
7441 aattttaaaa tatctgggaa gtcccttcca ctgctgtgtt ccagaagtgt tggtaaacag
7501 cccacaaatg tcaacagcag aaacatacaa gctgtcagct ttgcacaagg gccaacacc
7561 ctgctcatca agaagcactg tggttgctgt gttagtaatg tgcaaaacag gaggcacatt
7621 ttcccacct gtgtaggttc caaatatct agtgtttca ttttactg gatcaggaac
7681 ccagcactcc actgagataag cattatcctt atccaaaaca gccttgtggt cagtgttcat
7741 ctgctgactg tcaactgtag cattttttgg ggttacagtt tgagcaggat atttggtcct
7801 gtagtttgct aacacaccct gcagctccaa aggttcccca ccaacagcaa aaaaatgaaa
7861 atttgaccct tgaatgggt ttccagcacc atttttcatga gttttttgtg tccctgaatg
7921 caagtttaac atagcagtta cccaataac ctcagtttta acagtaacag cttcccacat
7981 caaaatattt ccacaggtta agtcctcatt taaattaggc aaaggaattc tt FIGURE 7 (continued)

STABLE CELL LINES FOR RETROVIRAL PRODUCTION

This application is a 371 of International Application No. PCT/EP2018/059917, filed 18 Apr. 2018, which claims priority to GB 1706121.9 filed 18 Apr. 2017, all of which are incorporated herein in their entireties.

FIELD OF THE INVENTION

The present invention relates to nucleic acid vectors comprising genes required for retroviral vector production and uses thereof. Also provided are methods of making retroviral packaging/producer cell lines comprising the nucleic acid vectors described herein.

BACKGROUND TO THE INVENTION

In gene therapy, genetic material is delivered to endogenous cells in a subject in need of treatment. The genetic material may introduce novel genes to the subject, introduce additional copies of pre-existing genes, or introduce different alleles or variants of genes that are present in the subject. Viral vector systems have been proposed as an effective gene delivery method for use in gene therapy (Verma and Somia (1997) *Nature* 389: 239-242).

In particular, these viral vectors are based on members of the retrovirus family due to their ability to integrate their genetic payload into the host's genome. Retroviral vectors are designed to keep the essential proteins required for packaging and delivery of the retroviral genome, but any non-essential accessory proteins including those responsible for their disease profile are removed. Examples of retroviral vectors include lentiviral vectors, such as those based upon Human Immunodeficiency Virus Type 1 (HIV-1), which are widely used because they are able to integrate into non-proliferating cells.

Currently, the majority of viral vectors are produced by transient co-transfection of viral genes into a host cell line. The viral genes are introduced using bacterial plasmids which exist in the host cell for only a limited period of time because the viral genes remain on the plasmids and are not integrated into the genome. As such, transiently transfected genetic material is not passed on to subsequent generations during cell division.

There are several drawbacks associated with transient transfection, such as batch-to-batch variability, the high cost of transfection reagents and the difficulty to maintain quality control (see Segura et al. (2013) *Expert Opin. Biol. Ther.* 13(7): 987-1011). The process of transfection itself is also labour-intensive and challenging to scale up. There is also the difficult task of removing plasmid impurities which are carried over during vector preparation (see Pichlmair et al. (2007) *J. Virol.* 81(2): 539-47).

In order to address problems associated with transient transfection, there has been a desire to develop retroviral packaging and producer cell lines in order to simplify retroviral vector production.

Packaging cell lines have been generated by transfecting a cell line capable of packaging retroviral vectors with plasmids, where individual plasmids carry the retroviral packaging genes and unique eukaryotic selection markers. The retroviral packaging genes are integrated into the packaging cell line's genome and are described as being stably transfected. Over the past 20 years various attempts have been made to generate stable packaging and producer cell lines for retroviral vectors.

There have been many reported problems in the packaging and producer cell lines produced via integration of retroviral vector components into the host cell genome. In the first instance, sequential introduction of retroviral vector components can be laborious and inflexible. There have also been problems with genetic and/or transcriptional instability of retroviral vector components when they are integrated into the host cell genome because the site of integration is unpredictable (Ni et al. (2005) *J. Gene Med.* 7: 818-834.).

A significant drop in viral vector productivity has also been reported during suspension adaptation and scale-up of the producer cell lines (Farson et al. (2001) *Hum. Gene Ther.* 12: 981-997; Guy et al. (2013) *Hum. Gene Ther. Methods.* 24(2): 125-39).

Attempts have also been made, within the biopharmaceutical industry, to produce transfected cell lines providing reliably high titres of recombinant proteins. Such processes typically involve screening transfected cells to identify cell lines with optimal growth and production of the recombinant protein (e.g. see Wurm, 2004, *Nature Biotechnology* 22, 1393-1398).

A known method involves selecting for a stably transfected cell line in which the recombinant gene of interest has been integrated into the genome of the host cell and amplified, such that the cell line comprises an increased copy number of the recombinant gene of interest. This is done by co-transfecting the host cell with a recombinant gene of interest together with an amplifiable selection marker gene that is inhibited by a known toxic drug. The stably transfected cells are then subjected to increasing concentrations of the known toxic drug, for example, by culturing the transfected cells in a medium containing the toxic drug. In this way, populations of transfected cells may be selected that have an increased copy number of the amplifiable selection marker gene through gene amplification, resulting in increased expression levels of the amplifiable selection marker and, thereby, conferring resistance to the toxic drug. As the process of gene amplification results in the amplification of the amplifiable selection marker and surrounding DNA sequences, in the event a recombinant gene of interest is integrated adjacent to the gene encoding the amplifiable selection marker within the host cell genome, it is possible to co-amplify nucleic acid sequences encoding the recombinant gene of interest, together with those encoding the amplifiable selection marker. This process relies on in vivo ligation and integration into the host cell genome of the amplifiable selection marker gene and the recombinant gene of interest (Kaufman, et al. 1985, *Mol. Cell. Biol.* 5: 1750-1759).

Given that the currently available methods for obtaining stably transfected packaging and producer cell lines for retroviral vector production requires sequential integration of the retroviral genes into the host cell genome and that the site of each integration event is random and unpredictable, it would be extremely difficult to obtain a cell line wherein all of the retroviral genes have been integrated in the vicinity of the amplifiable selection marker gene to obtain a cell line wherein the retroviral genes have been amplified. Therefore, it is envisaged that it will not be practicable to employ established selection procedures using amplifiable selection markers to select cell lines producing high titres of viral vectors.

It is therefore an object of the present invention to provide a method of making stable retroviral packaging and producer cell lines which overcomes one or more of the disadvantages associated with existing methods.

SUMMARY OF THE INVENTION

The present inventors have developed a new way of making retroviral packaging and producer cell lines which involves the use of nucleic acid vectors comprising a non-mammalian origin of replication and the ability to hold at least 25 kilobases (kb) of DNA, such as bacterial artificial chromosomes, comprising the retroviral genes essential for retroviral vector production and an amplifiable selection marker gene. This allows expression of the retroviral genes required for production of replication defective retroviral vector particles to ameliorate problems associated with transient transfection methods. Furthermore, as all of the essential retroviral genes and the amplifiable selection marker gene are transfected into a host cell in a single nucleic acid vector, the nucleic acid vector is integrated into the host genome in a single locus. This ameliorates problems associated with sequential transfection causing integration of the retroviral genes at different loci within the host genome, as well as the problems associated with using amplifiable selection markers to amplify the retroviral genes in said cells The use of a nucleic acid vector comprising a non-mammalian origin of replication and which has the ability to hold at least 25 kb of DNA (i.e. large-construct DNA) has several advantages. In the first instance, the vectors can first be manipulated in non-mammalian cells (e.g. microbial cells, such as bacterial cells) rather than mammalian host cells which makes them much easier to use (e.g. bacterial artificial chromosomes can first be manipulated in *E. coli*). Once the nucleic acid vector has been prepared, it can be introduced into a mammalian host cell and any mammalian cells which have the nucleic acid vector integrated into the endogenous chromosomes can be selected in order to isolate a stable cell line.

Introduction of the retroviral nucleic acids into the mammalian host cell also occurs in a single step which helps to reduce selection pressure and silencing timeframe. This allows for faster screening of potential packaging and producer cells and reduces the cost of materials because only a single vector is used, rather than previous methods which use multiple plasmid vectors. In particular, use of the current system reduces the cost of manufacture by saving on plasmid costs, transfection reagents required (e.g. Polyethylenimine [PEI]), reducing the amount of Benzonase treatment required (there is a reduced amount of DNA in the lentiviral harvest, therefore less Benzonase is needed to remove the excess in downstream processing) and reduced cost of testing (there is no need to test for residual plasmid in the lentiviral product).

Furthermore, the retroviral genes essential for retroviral production (with or without the transfer vector) and the amplifiable selection marker gene are present within the nucleic acid vector so that when the vector is introduced into mammalian host cells, all of the retroviral genes and the amplifiable selection marker gene will integrate at one locus within the mammalian host cell genome. This can overcome problems, such as gene silencing, which can occur when the retroviral genes are integrated randomly and at different loci within the host cell genome. This also provides a procedure for producing a packaging or producer cell with a high titre of retroviral vector particle, wherein amplification of the retroviral genes is not reliant on in vivo ligation of the retroviral genes to the amplifiable selection marker.

Therefore, according to a first aspect of the invention, there is provided a retroviral packaging cell comprising nucleic acid sequences encoding:
  gag and pol proteins;
  env protein or a functional substitute thereof; and
  an amplifiable selection marker;
  as individual expression constructs, wherein said expression constructs are all integrated together at a single locus within the retroviral packaging cell genome as a unit; and
  wherein the copy number of the unit is two or more.

In a further aspect of the invention, there is provided a retroviral producer cell comprising nucleic acid sequences encoding:
  gag and pol proteins;
  env protein or a functional substitute thereof;
  an amplifiable selection marker; and
  an RNA genome of a retroviral vector particle
  as individual expression constructs, wherein said expression constructs are all integrated together at a single locus within the retroviral producer cell genome as a unit; and
  wherein the copy number of the unit is two or more.

In an alternative aspect of the invention, there is provided a nucleic acid vector comprising a non-mammalian origin of replication and the ability to hold at least 25 kilobases (kb) of DNA, characterized in that said nucleic acid vector comprises nucleic acid sequences encoding:
  gag and pol proteins,
  an env protein or a functional substitute thereof, and
  an amplifiable selection marker
  wherein each of the nucleic acid sequences are arranged as individual expression constructs within the nucleic acid vector.

In yet a further aspect of the invention, there is provided a method of producing a stable retroviral packaging cell line, comprising the steps of:
  (a) transfecting the nucleic acid vector defined herein into a culture of mammalian host cells;
  (b) growing the transfected mammalian host cells in a medium which contains a concentration of a selection agent that inhibits the growth of the transfected mammalian cells which express insufficient levels of the amplifiable selection marker; and
  (c) selecting transfected mammalian host cells capable of growth in said medium, wherein the selected transfected mammalian host cells contain an amplified number of copies of the nucleic acid vector integrated into the transfected mammalian host cell genome.

In an alternative aspect of the invention, there is provided a retroviral packaging cell obtained by the method described herein.

In a further aspect of the invention, there is provided a method of producing a stable retroviral producer cell line, comprising the steps of:
  (a) transfecting the nucleic acid vector defined herein into a culture of mammalian host cells;
  (b) growing the transfected mammalian host cells in a medium which contains a concentration of a selection agent that inhibits the growth of the transfected mammalian host cells which express insufficient levels of the amplifiable selection marker; and
  (c) selecting transfected mammalian host cells capable of growth in said medium, wherein the selected transfected mammalian host cells contain an amplified number of copies of the nucleic acid vector integrated into the transfected mammalian host cell genome.

In yet a further aspect of the invention, there is provided a retroviral producer cell obtained by the method described herein.

In an alternative aspect of the invention, there is provided a method of producing a replication defective retroviral vector particle, comprising the steps of:

(a) transfecting the nucleic acid vector defined herein into a culture of mammalian host cells;

(b) growing the transfected mammalian host cells in a medium which contains a concentration of a selection agent that inhibits the growth of the transfected mammalian host cells which express insufficient levels of the amplifiable selection marker;

(c) selecting transfected mammalian host cells capable of growth in said medium, wherein the selected transfected mammalian host cells contain an amplified number of copies of the nucleic acid vector integrated into the transfected mammalian host cell genome; and (d) further culturing the mammalian host cells selected in step (c) under conditions in which the replication defective retroviral vector particle is produced.

In a further aspect of the invention, there is provided a replication defective retroviral vector particle obtained by the method described herein.

FIGURES

FIG. 1: A stepwise guide to the construction of BACpack-WTGP-277delU5 and BACpack-SYNGP-277delU5.

Figure 2:
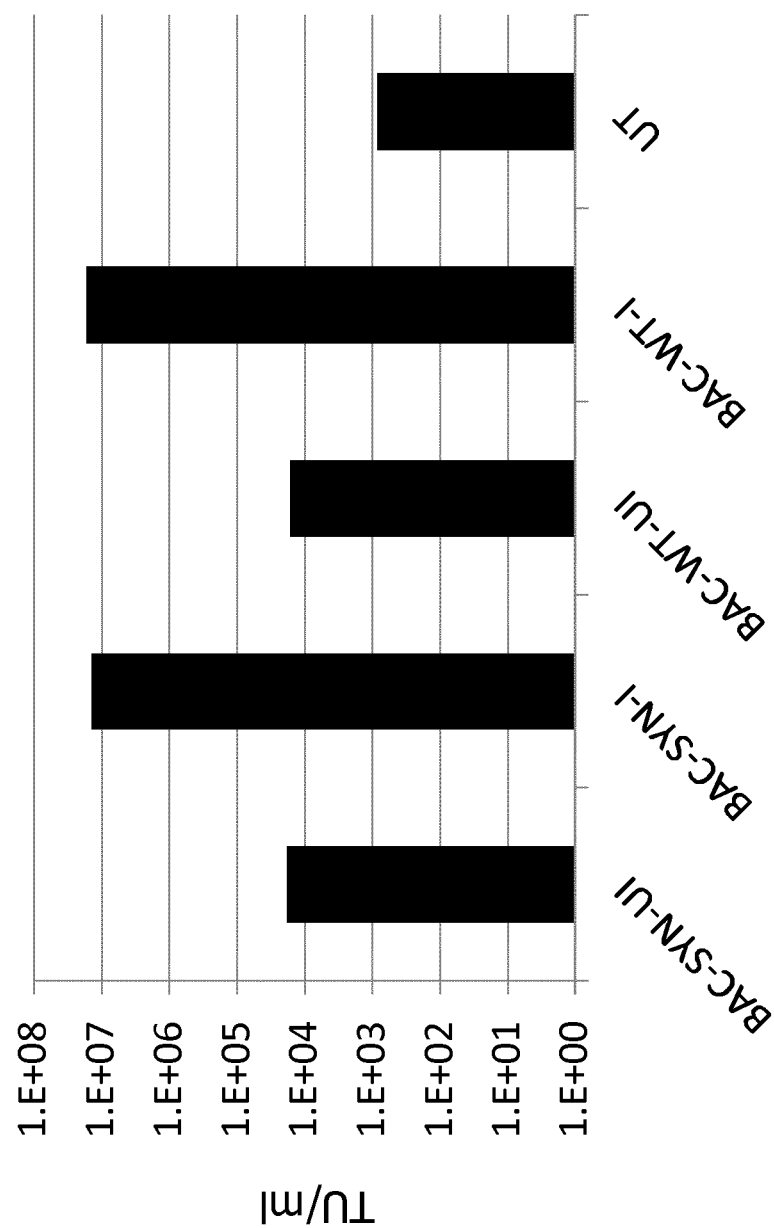

FIG. 2: Selection of a stable polyclonal pool. HEK293T adherent cells were transfected with BACpackWTGagPol-Transfer using Calcium Phosphate. Stable pools were generated after 2 weeks' Zeocin selection. To see whether the stable transfectants were capable of generating virus, the stable poly-pools were induced with Doxycycline for 48 hours. Viral supernatant was harvested 48 hours post induction, filtered through a 0.22 μm filter and titrated by transducing HEK293T cells. GFP positive transduced cells were used to calculate the Transducing Units/rd (TU/mL).

FIG. 3: Generating stable transfection suspension clones. HEK293 6E cells were transfected with BACpackWT-GagPol-Transfer using 293fectin reagent. Stable pools were generated after 2 weeks' Zeocin selection. The stable pools were cloned by limiting dilution into 96 well plates to obtain single cell clones, which were subsequently expanded. GFP detected by fluorescence microscopy of the best clones 1, 14, 15 and 16, obtained with adherent medium (DMEM+FBS) followed by suspension adaptation (FreeStyle medium).

Figure 4:
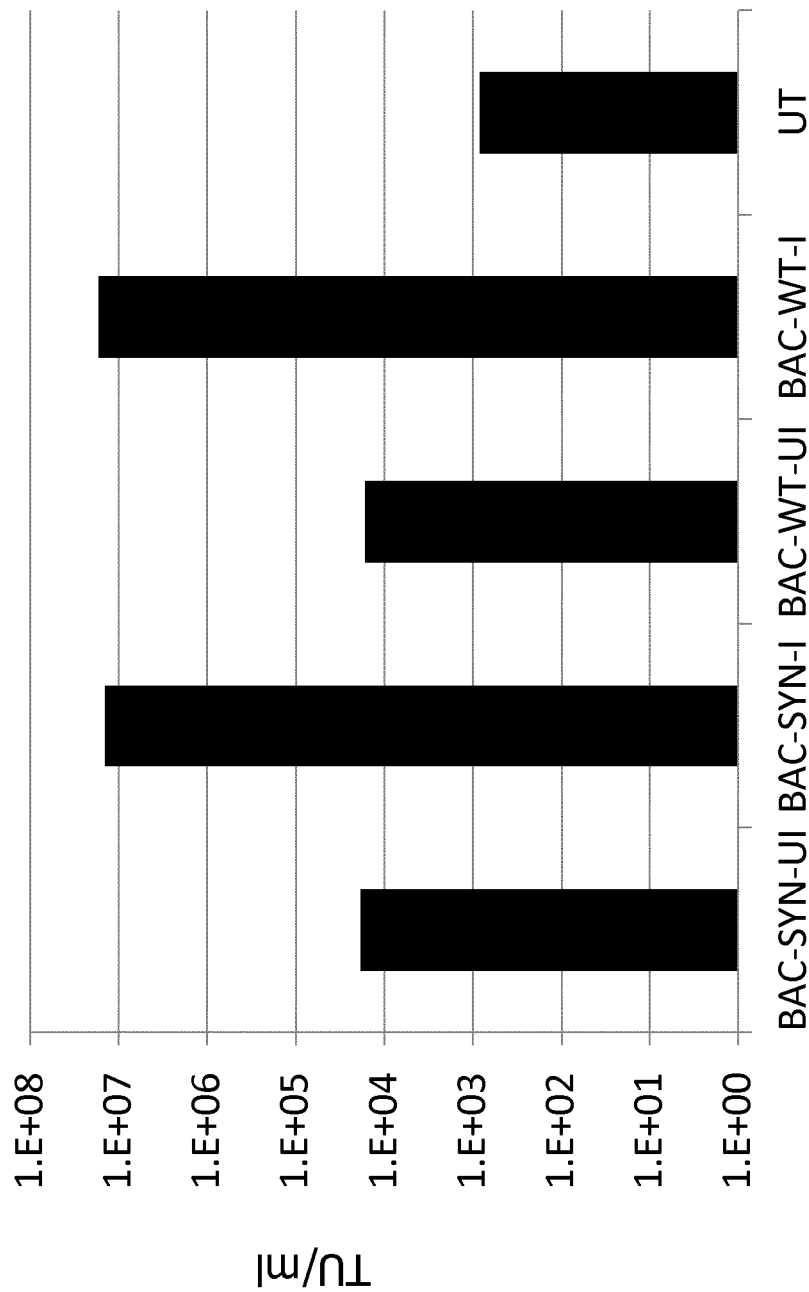

FIG. 4: Induction of Lentivirus in the suspension clones. To see whether the stable HEK6E transfectants were capable of generating virus, 20 ml of the stable suspension clones were induced with Doxycycline (2 μg/ml) for 48 hours. Viral supernatant was harvested 48 hours post induction, filtered through a 0.45 μm filter and titrated by transducing HEK293T cells. GFP positive transduced cells were used to calculate the Transducing Units/ml (TU/mL).

FIG. 5: Vector titres of clones produced according to Example 4. Results show vector titres from clones 1 and 16 increased modestly between passage 5 and passage 21.

Figure 6:
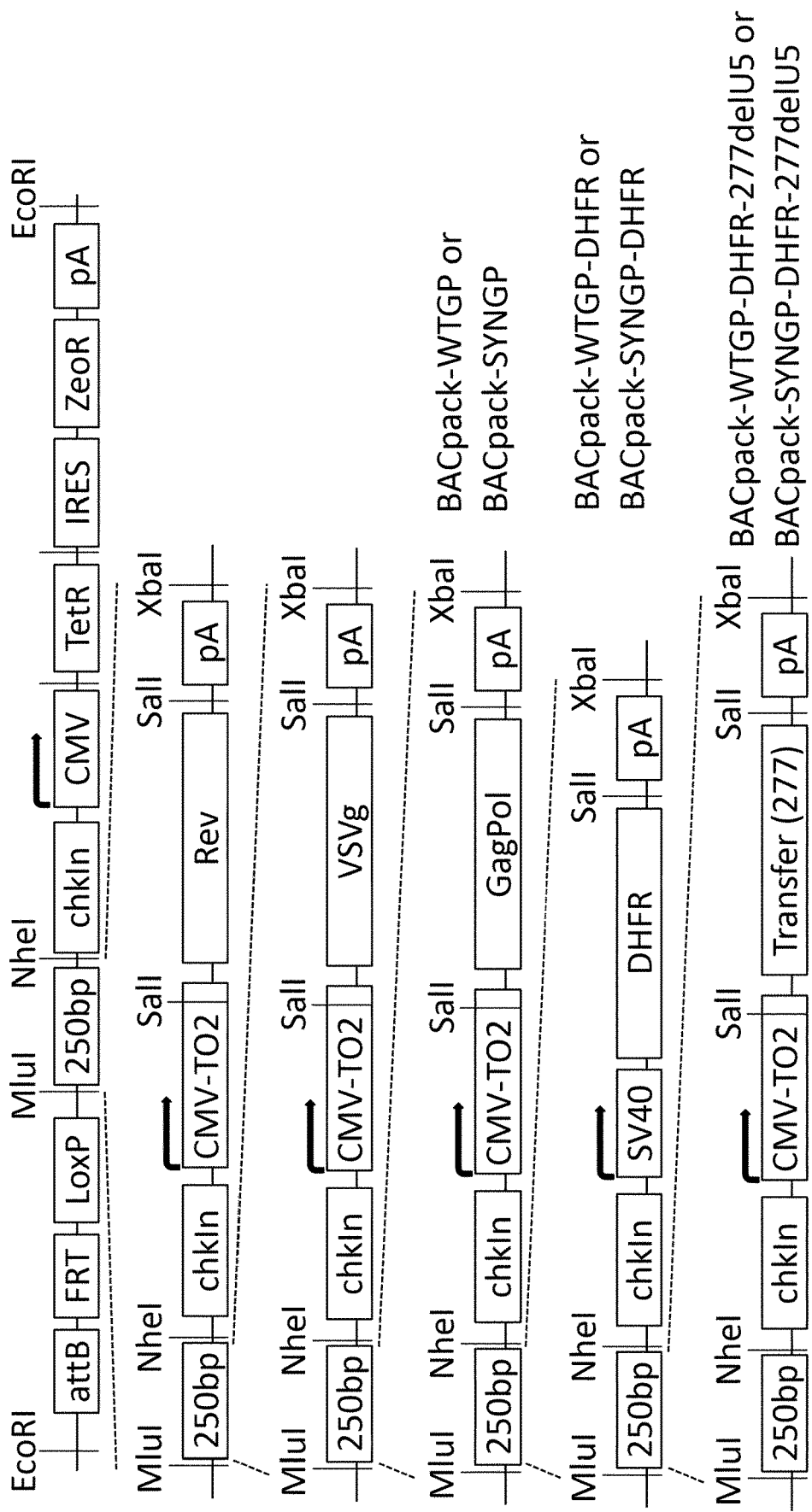

FIG. 6: A stepwise guide to the construction of BACpack-WTGP-DHFR-277delU5 and BACpack-SYNGP-DHFR-277delU5.

FIG. 7: Nucleic acid sequence of an expression construct comprising a dhfr gene (SEQ ID NO: 1).

Figure 8:
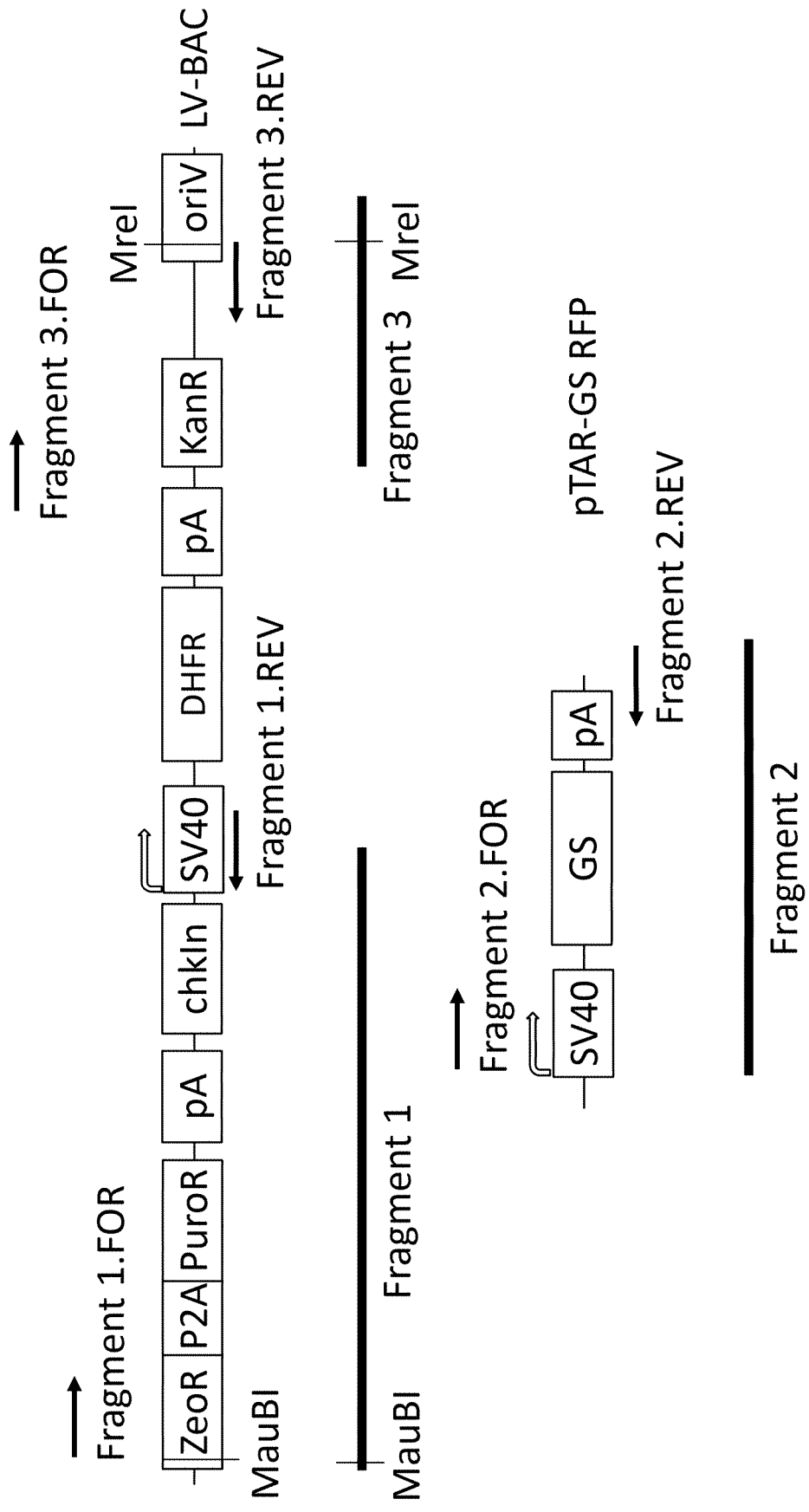
Figure 8:
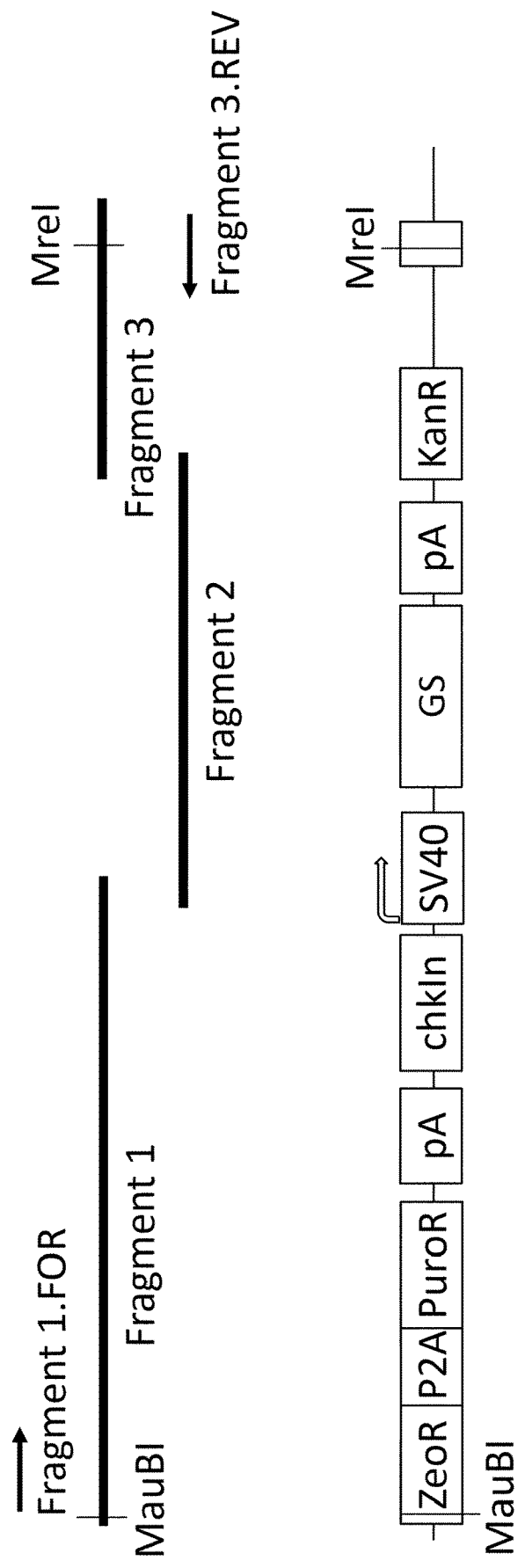
Figure 8:
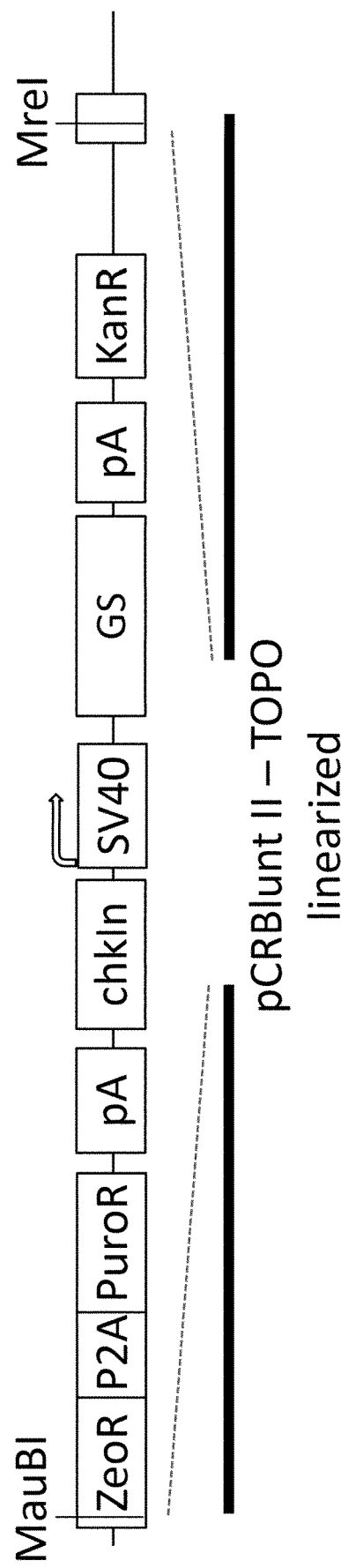
Figure 8:
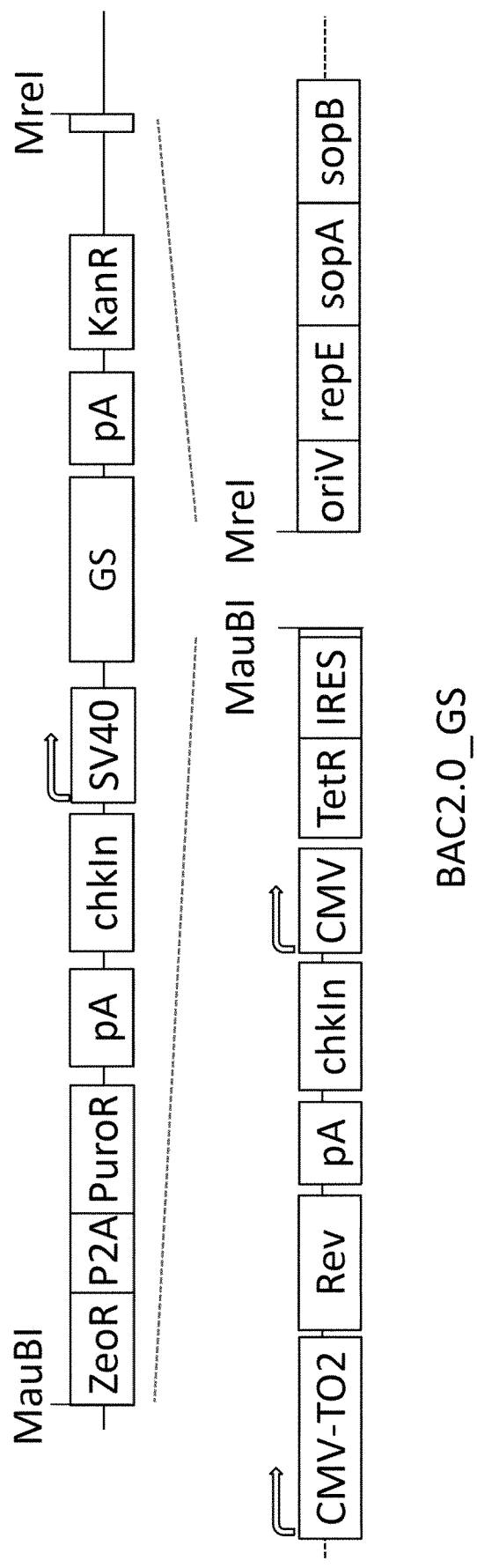

FIG. 8: A stepwise guide to the construction of BAC2.0 GS.

DETAILED DESCRIPTION OF THE INVENTION

Definitions

Unless defined otherwise, all technical and scientific terms used herein have the same meaning as is commonly understood by one of skill in the art to which this invention belongs. All patents and publications referred to herein are incorporated by reference in their entirety.

The term "comprising" encompasses "including" or "consisting" e.g. a composition "comprising" X may consist exclusively of X or may include something additional e.g. X+Y.

The term "consisting essentially of" limits the scope of the feature to the specified materials or steps and those that do not materially affect the basic characteristic(s) of the claimed feature.

The term "consisting of" excludes the presence of any additional component(s).

The term "about" in relation to a numerical value x means, for example, x±10%, 5%, 2% or 1%.

The term "vector" or "nucleic acid vector" refers to a vehicle which is able to artificially carry foreign (i.e. exogenous) genetic material into another cell, where it can be replicated and/or expressed. Examples of vectors include non-mammalian nucleic acid vectors, such as bacterial artificial chromosomes (BACs), yeast artificial chromosomes (YACs), P1-derived artificial chromosomes (PACs), cosmids or fosmids. The term "nucleic acid vector" as used herein in the context of integration into a host cell genome, refers to the DNA originating from the nucleic acid vector that has been integrated into a host cell's genome.

Other examples of vectors include viral vectors, such as retroviral and lentiviral vectors, which are of particular interest in the present application. Lentiviral vectors, such as those based upon Human Immunodeficiency Virus Type 1 (HIV-1) are widely used as they are able to integrate into non-proliferating cells. Viral vectors can be made replication defective by splitting the viral genome into separate parts, e.g., by placing on separate plasmids. For example, the so-called first generation of lentiviral vectors, developed by the Salk Institute for Biological Studies, was built as a three-plasmid expression system consisting of a packaging expression cassette, the envelope expression cassette and the transfer vector expression cassette. The "packaging plasmid" contains the entire gag pol sequences, the regulatory (tat at and rev) and the accessory (vif, vpr, vpu, net) sequences. The "envelope plasmid" holds the Vesicular stomatitis virus glycoprotein (VSVg) in substitution for the native HIV-1 envelope protein, under the control of a cytomegalovirus (CMV) promoter. The third plasmid (the "transfer plasmid" or "transfer vector") carries between the Long Terminal Repeats (LTRs), the transgene, encapsulation sequence (ψ), the Rev Response Element (RRE) sequence and the CMV promoter to express the transgene inside the host cell.

The second lentiviral vector generation was characterized by the deletion of the virulence sequences vpr, vif, vpu and nef. The packaging vector was reduced to gag, pol, tat and rev genes, therefore increasing the safety of the system.

To improve the lentiviral system, the third-generation vectors have been designed by removing the tat gene from the packaging construct and inactivating the LTR from the vector cassette, therefore reducing problems related to insertional mutagenesis effects.

The various lentivirus generations are described in the following references: First generation: Naldini et al. (1996) *Science* 272(5259): 263-7; Second generation: Zufferey et al. (1997) *Nat. Biotechnol.* 15(9): 871-5; Third generation: Dull et al. (1998) *J. Virol.* 72(11): 8463-7, all of which are incorporated herein by reference in their entirety. A review on the development of lentiviral vectors can be found in Sakuma et al. (2012) *Biochem. J.* 443(3): 603-18 and Picanço-Castro et al. (2008) *Exp. Opin. Therap. Patents* 18(5): 525-539.

The term "non-mammalian origin of replication" refers to a nucleic acid sequence where replication is initiated and which is derived from a non-mammalian source. This enables the nucleic acid vectors of the invention to stably replicate and segregate alongside endogenous chromosomes in a suitable host cell (e.g. a microbial cell, such as a bacterial or yeast cell) so that it is transmittable to host cell progeny, except when the host cell is a mammalian host cell. In mammalian host cells, nucleic acid vectors with non-mammalian origins of replication will either integrate into the endogenous chromosomes of the mammalian host cell or be lost upon mammalian host cell replication. For example, nucleic acid vectors with non-mammalian origins of replication such as bacterial artificial chromosomes (BAC), P1-derived artificial chromosome (PAC), cosmids or fosmids, are able to stably replicate and segregate alongside endogenous chromosomes in bacterial cells (such as *E. coli*), however, if they are introduced into mammalian host cells, the BAC, PAC, cosmid or fosmid will either integrate or be lost upon mammalian host cell replication. Yeast artificial chromosomes (YAC) are able to stably replicate and segregate alongside endogenous chromosomes in yeast cells, however, if they are introduced into mammalian host cells, the YAC will either integrate or be lost upon mammalian host cell replication. Therefore, in this context, the nucleic acid vectors of the invention act as reservoirs of DNA (i.e. for the genes essential for retroviral production) which can be easily transferred into mammalian host cells to generate stable cell lines for retroviral production. Examples of non-mammalian origins of replication include bacterial origins of replications, such as oriC, oriV or oriS, or yeast origins of replication, also known as Autonomously Replicating Sequences (ARS elements).

The nucleic acid vectors of the present invention comprise a non-mammalian origin of replication and are able to hold at least 25 kilobases (kb) of DNA. In one embodiment, the nucleic acid vector has the ability to hold at least 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340 or 350 kb of DNA. It will be understood that references to "ability to hold" has its usual meaning and implies that the upper limit for the size of insert for the nucleic acid vector is not less than the claimed size (i.e. not less than 25 kb of DNA).

The aim of the present invention is to include the genes essential for retroviral packaging and an amplifiable selection marker gene in a single construct (i.e. the nucleic acid vector). Therefore, the nucleic acid vector of the invention, must be able to hold large inserts of DNA. For the avoidance of doubt, it will be understood that references to "nucleic acid vectors" or "artificial chromosomes" do not refer to natural bacterial plasmids (e.g. such as the plasmids currently used in transient transfection methods) because these are not able to hold at least 25 kb of DNA. The maximum size insert which a plasmid can contain is about 15 kb. Such nucleic acid vectors also do not refer to bacteriophages which generally only hold maximum inserts of 5-11 kb. Therefore, in one embodiment the nucleic acid vector of the invention is not a plasmid, bacteriophage or episome.

The term "endogenous chromosomes" (or host cell genome) refers to genomic chromosomes found in the host cell prior to generation or introduction of an exogenous nucleic acid vector, such as a bacterial artificial chromosome.

The terms "transfection", "transformation" and "transduction" as used herein, may be used to describe the insertion of the non-mammalian or viral vector into a target cell (i.e. host cell). Insertion of a vector is usually called transformation for bacterial cells and transfection for eukaryotic cells, although insertion of a viral vector may also be called transduction. The skilled person will be aware of the different non-viral transfection methods commonly used, which include, but are not limited to, the use of physical methods (e.g. electroporation, cell squeezing, sonoporation, optical transfection, protoplast fusion, impalefection, magnetofection, gene gun or particle bombardment), chemical reagents (e.g. calcium phosphate, highly branched organic compounds or cationic polymers) or cationic lipids (e.g. lipofection). Many transfection methods require the contact of solutions of plasmid DNA to the cells, which are then grown and selected for a marker gene expression.

The term "promoter" refers to a sequence that drives gene expression. In order to drive a high level of expression, it may be beneficial to use a high efficiency promoter, such as a non-retroviral, high efficiency promoter. Examples of suitable promoters may include a promoter such as the human cytomegalovirus (CMV) immediate early promoter, spleen focus-forming virus (SFFV) promoter, Rous sarcoma virus (RSV) promoter, or human elongation factor 1-alpha (pEF) promoter.

A Tet operon (Tetracycline-Controlled Transcriptional Activation) may be used in a method of inducible gene expression, wherein transcription is reversibly turned on or off in the presence of the antibiotic tetracycline or one of its derivatives (e.g. doxycycline). In nature, the Ptet promoter expresses TetR, the repressor, and TetA, the protein that pumps tetracycline antibiotic out of the cell. In the present invention, the Tet operon may be present or absent, for example, in one embodiment the Tet operon may be present in the promoter.

The term "polyA signal" refers to a polyadenylation signal sequence, for example placed 3' of a transgene, which enables host factors to add a polyadenosine (polyA) tail to the end of the nascent mRNA during transcription. The polyA tail is a stretch of up to 300 adenosine ribonucleotides which protects mRNA from enzymatic degradation and also aids in translation. Accordingly, the nucleic acid vectors of the present invention may include a polyA signal sequence such as the human beta globin or rabbit beta globin polyA signals, the simian virus 40 (SV40) early or late polyA signals, the human insulin polyA signal, or the bovine growth hormone polyA signal. In one embodiment, the polyA signal sequence is the human beta globin polyA signal.

The term "intron sequence" refers to a nucleotide sequence which is removed from the final gene product by RNA splicing. The use of an intron downstream of the enhancer/promoter region and upstream of the cDNA insert has been shown to increase the level of gene expression. The increase in expression depends on the particular cDNA insert. Accordingly, the nucleic acid vector of the present invention may include introns such as human beta globin intron, rabbit beta globin intron II or a chimeric human beta globin-immunoglobulin intron. In one embodiment, the intron is a human beta globin intron and/or a rabbit beta globin intron II.

The term "packaging cell line" refers to a cell line with stably inserted gag and pol protein and envelope glycoprotein genes. Alternatively, the term "producer cell line" refers to a packaging cell line with a stably inserted "transfer vector" components (as used in transient transfection methods) containing a transgene of interest between the LTR sequences as described above. It will be understood by a person skilled in the art that the nucleic acid vectors described herein may be used to generate packaging cell lines (i.e. when at least the gag, pol and env genes are present on the nucleic acid vector and incorporated into a host cell) or producer cell lines (i.e. when the nucleic acid vector additionally comprises the transfer vector components to be incorporated into a host cell along with the gag, pol and envgenes).

The term "stably transfected" refers to cell lines which are able to pass introduced retroviral genes to their progeny (i.e. daughter cells), either because the transfected DNA has been incorporated into the endogenous chromosomes or via stable inheritance of exogenous chromosomes.

The terms "expression construct" and "expression cassette" are used interchangeably and as used herein refers to a functional expression unit, capable of driving the expression of one or more incorporated polynucleotides. Such cassettes usually include the polynucleotide and the components necessary for the transcription and translation of the polynucleotide. For example, the cassette may include a nucleic acid sequence (i.e. recombinant DNA) including a promoter, a translational initiation sequence signal, a transcriptional terminator (e.g. a polyA sequence) and/or a self-cleaving peptide sequence (e.g. P2A sequence). In one embodiment, the individual expression cassette comprises a promoter and/or a transcriptional terminator. In one embodiment, the individual expression cassette comprises two genes separated by an IRES that are both transcribed from a single promoter. The construct may also contain any other additional components known in the art which may enhance or provide greater control of the transcription and translation of the polynucleotide. In one embodiment, the additional components may be any nucleic acid sequences from the SV40 genome.

Nucleic Acid Vectors

According to one aspect of the invention, there is provided a nucleic acid vector comprising a non-mammalian origin of replication and the ability to hold at least 25 kilobases (kb) of DNA, characterized in that said nucleic acid vector comprises nucleic acid sequences encoding:
  gag and pol proteins,
  an env protein or a functional substitute thereof, and
  an amplifiable selection marker,
wherein each of the nucleic acid sequences are arranged as individual expression constructs within the nucleic acid vector.

Current methods for generating retroviral vector particles involve transient transfection of the retroviral genes into a host cell. However, many disadvantages have been associated with this method because it is costly, laborious and difficult to scale-up. One solution would be to engineer a packaging cell line that stably incorporates the retroviral packaging genes to avoid the problems associated with transient transfection.

The present inventors have found that nucleic acid vectors described herein can be used to generate a retroviral packaging or producer cell line which ameliorates previous difficulties associated with retroviral vector production methods. For example, known methods of producing retroviral packaging cell lines involve multiple rounds of selection after each retroviral gene is introduced. This process can take up to six months and is heavily labour intensive. Even after a packaging cell line is obtained after the long and laborious process, there have been reports of a significant drop in viral vector productivity during suspension adaptation and scale-up of the packaging cell lines.

By including all of the retroviral genes in the nucleic acid vector, the retroviral genes can then be inserted into the endogenous chromosome of a mammalian host cell in one single step. Therefore, the use of a nucleic acid vector, as proposed herein, would reduce selection pressure, reduce the silencing timeframe and allow for faster screening of potential packaging cells.

Furthermore, the retroviral genes of the nucleic acid vector would all be integrated into the endogenous chromosome of the mammalian host cell at a single locus which would reduce the risk of individual retroviral genes becoming silenced and allow all of the retroviral genes to be expressed evenly.

Integration at a single locus in the host cell's genome allows for a procedure for amplifying the retroviral genes using an amplifiable selection marker gene, wherein amplification of the retroviral genes is not reliant on in vivo ligation of the retroviral genes to the amplifiable selection marker as would be necessary if the retroviral genes were not integrated together in a single locus.

Therefore, by using the nucleic acid vector described herein, it is possible to select for a packaging or producer cell with amplified retroviral genes resulting in improved titre of retroviral vector particles.

In one embodiment, the nucleic acid vector additionally comprises nucleic acid sequences which encode the RNA genome of the retroviral vector particle. When this nucleic acid sequence is transcribed, it will become encapsidated within the retroviral vector particle produced by the cell and, therefore, act as the retroviral vector particle's genome. It will be understood that the nucleic acid sequences encoding the RNA genome of the retroviral vector particle is usually included on the "transfer vector" used in transient transfection methods. The transfer vector plasmid generally contains a promoter (such as SV40) operably linked to a transgene (and optionally a polyadenylation signal and, further optionally, nucleic acid sequences for controlling/enhancing transcription and expression of the transgene) and an encapsidation sequence (ψ) between two LTR sequences; the 3' LTR (which may or may not be a self-inactivating (i.e. SIN) 3'-LTR) and the 5' LTR (which may or may not contain the U5 region). Therefore, in one embodiment, the RNA genome of the retroviral vector particle comprises one or more transgenes encoded between two LTRs.

In one embodiment, multiple copies of the nucleic acid sequences which encode the RNA genome of the retroviral vector particle (i.e. components of the "transfer vector") are included in the nucleic acid vector. Multiple copies of the transfer vector are expected to result in a higher viral vector titre. For example, the nucleic acid vector may include two or more, such as three, four, five, six, seven, eight, nine or ten or more copies of the nucleic acid sequences encoding the RNA genome of the retroviral vector particle (i.e. the transfer vector).

In one embodiment, the nucleic acid vector contains one or a plurality of recombination site(s). This allows for target sequences to be integrated into the endogenous chromosomes of the mammalian host cell in a site-specific manner in the presence of a recombinase enzyme. The recombinase enzyme catalyses the recombination reaction between two recombination sites.

Many types of site-specific recombination systems are known in the art, and any suitable recombination system may be used in the present invention. For example, in one embodiment the recombination site(s) are selected or derived from the int/att system of lambda phage, the Cre/lox system of bacteriophage P1, the FLP/FRT system of yeast, the Gin/gix recombinase system of phage Mu, the Cin recombinase system, the Pin recombinase system of *E. coli* and the R/RS system of the pSR1 plasmid, or any combination thereof. In a further embodiment, the recombination site is an att site (e.g. from lambda phage), wherein the att site permits site-directed integration in the presence of a lambda integrase. It will be understood that the reference to "lambda integrase" includes references to mutant integrases which are still compatible with the intI att system, for example the modified lambda integrases described in WO 2002/097059.

In one embodiment, the nucleic acid vector is selected from: a bacterial artificial chromosome (BAC), a yeast artificial chromosome (YAC), a P1-derived artificial chromosome (PAC), fosmid or a cosmid. In a further embodiment, the nucleic acid vector is a bacterial artificial chromosome (BAC).

Bacterial Artificial Chromosomes

The term "bacterial artificial chromosome" or "BAC" refers to a DNA construct derived from bacterial plasmids which is able to hold a large insert of exogenous DNA. They can usually hold a maximum DNA insert of approximately 350 kb. BACs were developed from the well characterised bacterial functional fertility plasmid (F-plasmid) which contains partition genes that promote the even distribution of plasmids after bacterial cell division. This allows the BACs to be stably replicated and segregated alongside endogenous bacterial genomes (such as E. co/i). The BAC usually contains at least one copy of an origin of replication (such as the oriS or oriVgene), the repEgene (for plasmid replication and regulation of copy number) and partitioning genes (such as sopA, sopB, parA, parB and/or parC) which ensures stable maintenance of the BAC in bacterial cells. BACs are naturally circular and supercoiled which makes them easier to recover than linear artificial chromosomes, such as YACs. They can also be introduced into bacterial host cells relatively easily, using simple methods such as electroporation.

In one embodiment, the bacterial artificial chromosome comprises an oriS gene. In one embodiment, the bacterial artificial chromosome comprises a repE gene. In one embodiment, the bacterial artificial chromosome comprises partitioning genes. In a further embodiment, the partitioning genes are selected from sopA, sopB, parA, parB and/or parC In a yet further embodiment, the bacterial artificial chromosome comprises a sopA and sopB gene.

BAC for use in the present invention may be obtained from commercial sources, for example the pSMART BAC from LUCIGEN™ (see Genome Accession No. EU101022.1 for the full back bone sequence). This BAC contains the L-arabinose "copy-up" system which also contains the oriV medium-copy origin of replication, which is active only in the presence of the TrfA replication protein. The gene for TrfA may be incorporated into the genome of bacterial host cells under control of the L-arabinose inducible promoter araC-P, BAD (see Wild et al. (2002) *Genome Res.* 12(9): 1434-1444). Addition of L-arabinose induces expression of TrfA, which activates oriV, causing the plasmid to replicate to up to 50 copies per cell.

Yeast Artificial Chromosomes

The term "yeast artificial chromosome" or "YAC" refers to chromosomes in which yeast DNA is incorporated into bacterial plasmids. They contain an autonomous replication sequence (ARS) (i.e. an origin of replication), a centromere and telomeres. Unlike BACs, the YAC is linear and therefore contains yeast telomeres at each end of the chromosome to protect the ends from degradation as it is passed onto host cell progeny. YACs can hold a range of DNA insert sizes; anything from 100-2000 kb.

P1-Derived Artificial Chromosomes

The term "P1-derived artificial chromosome" or "PAC" refers to DNA constructs derived from the DNA of the P1-bacteriophage and bacterial F-plasmid. They can usually hold a maximum DNA insert of approximately 100-300 kb and are used as cloning vectors in *E. coli*: PACs have similar advantages as BACs, such as being easy to purify and introduce into bacterial host cells.

Cosmids and Fosmids

The term "cosmid" refers to DNA constructs derived from bacterial plasmids which additionally contain cos sites derived from bacteriophage lambda. Cosmids generally contain a bacterial origin of replication (such as oriV), a selection marker, a cloning site and at least one cos site. Cosmids can usually accept a maximum DNA insert of 40-45 kb. Cosmids have been shown to be more efficient at infecting *E. coli* cells than standard bacterial plasmids. The term "fosmids" refers to non-mammalian nucleic acid vectors which are similar to cosmids, except that they are based on the bacterial F-plasmid. In particular, they use the F-plasmid origin of replication and partitioning mechanisms to allow cloning of large DNA fragments. Fosmids can usually accept a maximum DNA insert of 40 kb.

Retroviruses

Retroviruses are a family of viruses which contain a pseudo-diploid single-stranded RNA genome. They encode a reverse transcriptase which produces DNA from the RNA genome which can then be inserted into the host cell DNA. The invention described herein may be used to produce replication defective retroviral vector particles. The retroviral vector particle of the present invention may be selected from or derived from any suitable retrovirus.

In one embodiment, the retroviral vector particle is derived from, or selected from, a lentivirus, alpha-retrovirus, gamma-retrovirus or foamy-retrovirus, such as a lentivirus or gamma-retrovirus, in particular a lentivirus. In a further embodiment, the retroviral vector particle is a lentivirus selected from the group consisting of HIV-1, HIV-2, SIV, FIV, EIAV and Visna. Lentiviruses are able to infect non-dividing (i.e. quiescent) cells which makes them attractive retroviral vectors for gene therapy. In a yet further embodiment, the retroviral vector particle is HIV-1 or is derived from HIV-1. The genomic structure of some retroviruses may be found in the art. For example, details on HIV-1 may be found from the NCBI Genbank (Genome Accession No. AF033819). HIV-1 is one of the best understood retroviruses and is therefore often used as a retroviral vector.

Retroviral Genes

The nucleic acid sequences common to all retroviruses may be explained in more detail, as follows:

Long Terminal Repeats (LTRs): The basic structure of a retrovirus genome comprises a 5'-LTR and a 3'-LTR, between or within which are located the genes required for retroviral production. The LTRs are required for retroviral integration and transcription. They can also act as promoter sequences to control the expression of the retroviral genes (i.e. they are cis-acting genes). The LTRs are composed of three sub-regions designated U3, R, U5: U3 is derived from the sequence unique to the 3' end of the RNA; R is derived from a sequence repeated at both ends of the RNA; and U5 is derived from the sequence unique to the 5' end of the RNA. Therefore, in one embodiment, the nucleic acid vector additionally comprises a 5'- and 3'-LTR. In a further embodiment, the U5 region of the 5' LTR can be deleted and replaced with a non-HIV-1 polyA tail (see Hanawa et al. (2002) *Mol. Ther* 5(3): 242-51).

In order to address safety concerns relating to the generation of replication-competent virus, a self-inactivating (SIN) vector has been developed by deleting a section in the U3 region of the 3' LTR, which includes the TATA box and binding sites for transcription factors Sp1 and NF-κB (see Miyoshi et al. (1998) *J. Virol* 72(10): 8150-7). The deletion is transferred to the 5' LTR after reverse transcription and integration in infected cells, which results in the transcriptional inactivation of the LTR. This is known as a self-inactivating lentiviral-based vector system which may be included in the present invention.

ψ: Encapsidation of the retroviral RNAs occurs by virtue of a y (psi) sequence located at the 5' end of the retroviral genome. It is also well known in the art that sequences downstream of the psi sequence and extending into the gag coding region are involved in efficient retroviral vector production (see Cui et al. (1999) *J. Virol* 73(7): 6171-6176). In one embodiment, the nucleic acid vector additionally comprises a y (psi) sequence.

Primer Binding Site (PBS): The retroviral genome contains a PBS which is present after the U5 region of the 5'-LTR. This site binds to the tRNA primer required for initiation of reverse transcription. In one embodiment, the nucleic acid vector additionally comprises a PBS sequence.

PPT: Retroviral genomes contain short stretches of purines, called polypurine tracts (PPTs), near the 3' end of the retroviral genome. These PPTs function as RNA primers for plus-strand DNA synthesis during reverse transcription. Complex retroviruses (such as HIV-1) contain a second, more centrally located PPT (i.e. a central polypurine tract (cPPT)) that provides a second site for initiation of DNA synthesis. Retroviral vectors encoding a cPPT have been shown to have enhanced transduction and transgene expression (see Barry et al. (2001) *Hum. Gene Ther.* 12(9): 1103-8). In one embodiment, the nucleic acid vector additionally comprises a 3'-PPT sequence and/or a cPPT sequence.

The genomic structure of the non-coding regions described above are well known to a person skilled in the art. For example, details on the genomic structure of the non-coding regions in HIV-1 may be found from the NCBI Genbank with Genome Accession No. AF033819, or for HIV-1 HXB2 (a commonly used HIV-1 reference strain) with Genome Accession No. K03455. In one embodiment, the non-coding regions are derived from the sequences available at Genome Accession No. K03455, for example from base pairs 454-1126 (for R-U5-PBS-Gag), 7622-8479 (for RRE) or 7769-8146 (for RRE), 4781-4898 (for cPPT), 9015-9120 & 9521-9719 (for dNEF-PPT-sinU3-R-U5).

Gag/pol. The expression of gag and pol genes relies on a translational frameshift between gag and gagpol. Both are polyproteins which are cleaved during maturation. The major structural matrix, capsid, and nucleocapsid proteins of the retroviral vector are encoded by gag. The pot gene codes for the retroviral enzymes: i) reverse transcriptase, essential for reverse transcription of the retroviral RNA genome to double stranded DNA, ii) integrase, which enables the integration of the retroviral DNA genome into a host cell chromosome, and iii) protease, that cleaves the synthesized polyprotein in order to produce the mature and functional proteins of the retrovirus. In one embodiment, the retroviral nucleic acid sequence encoding the gag and pol proteins is derived from the HIV-1 HXB2 sequence, which is available at Genome Accession No. K03455, for example from base pairs 790-5105.

Env. The env ("envelope") gene codes for the surface and transmembrane components of the retroviral envelope (e.g. glycoproteins gp120 and gp41 of HIV-1) and is involved in retroviral-cell membrane fusion. In order to broaden the retroviral vector's tissue tropism, the retroviral vectors described herein may be pseudotyped with an envelope protein from another virus. Pseudotyping refers to the process whereby the host cell range of retroviral vectors, including lentiviral vectors, can be expanded or altered by changing the glycoproteins (GPs) on the retroviral vector particles (e.g. by using GPs obtained from or derived from other enveloped viruses or using synthetic/artificial GPs). The most commonly used glycoprotein for pseudotyping retroviral vectors is the Vesicular stomatitis virus GP (VSVg), due to its broad tropism and high vector particle stability. However, it will be understood by the skilled person that other glycoproteins may be used for pseudotyping (see Cronin et al. (2005) *Curr. Gene Ther.* 5(4): 387-398, herein incorporated by reference in its entirety). The choice of virus used for pseudotyping may also depend on the type of cell and/or organ to be targeted because some pseudotypes have been shown to have tissue-type preferences. In one embodiment, the functional substitute of env protein is a Vesicular stomatitis virus glyprotein.

In one embodiment, the env protein or a functional substitute thereof is obtained from or derived from a virus selected from a Vesiculovirus (e.g. Vesicular stomatitis virus), Lyssavirus (e.g. Rabies virus, Mokola virus), Arenavirus (e.g. Lymphocytic choriomeningitis virus (LCMV)), Alphavirus (e.g. Ross River virus (RRV), Sindbis virus, Semliki Forest virus (SFV), Venezuelan equine encephalitis virus), Filovirus (e.g. Ebola virus Reston, Ebola virus Zaire, Lassa virus), Alpharetrovirus (e.g. Avian leukosis virus (ALV)), Betaretrovirus (e.g. Jaagsiekte sheep retrovirus (JSRV)), Gammaretrovirus (e.g. Moloney Murine leukaemia virus (MLV), Gibbon ape leukaemia virus (GALV), Feline endogenous retrovirus (RD114)), Deltaretrovirus (e.g. Human T-lymphotrophic virus 1 (HTLV-1)), Spumavirus (e.g. Human foamy virus), Lentivirus (e.g. Maedi-visna virus (MW)), Coronavirus (e.g. SARS-CoV), Respirovirus (e.g. Sendai virus, Respiratory syncytia virus (RSV)), Hepacivirus (e.g. Hepatitis C virus (HCV)), Influenzavirus (e.g. Influenza virus A) and Nucleopolyhedrovirus (e.g. *Autographa californica* multiple nucleopolyhedrovirus (AcMNPV)). In a further embodiment, the env protein or a functional substitute thereof is obtained from or derived from Vesicular stomatitis virus. In this embodiment, the Vesicular stomatitis virus glycoprotein (VSVg) protein may be used which enables the retroviral particles to infect a broader host cell range and eliminates the chances of recombination to produce wild-type envelope proteins. In a further embodiment, the retroviral nucleic acid sequence encoding the env protein or a functional substitute thereof, is derived from the sequence available at Genome Accession No. J02428.1, for example from base pairs 3071 to 4720.

The structural genes described herein are common to all retroviruses. Further auxiliary genes may be found in different types of retrovirus. For example, lentiviruses, such as HIV-1, contain six further auxiliary genes known as rev, vif, vpu, vpr, nef and tat Other retroviruses may have auxiliary genes which are analogous to the genes described herein, however they may not have always been given the same name as in the literature. References such as Tomonaga and Mikami (1996) *J. Gen. Virol.* 77(Pt 8): 1611-1621 describe various retrovirus auxiliary genes.

Rev: The auxiliary gene rev ("regulator of virion") encodes an accessory protein which binds to the Rev Response element (RRE) and facilitates the export of retroviral transcripts. The gene's protein product allows fragments of retroviral mRNA that contain the Rev Responsive element (RRE) to be exported from the nucleus to the cytoplasm. The RRE sequence is predicted to form a complex folded structure. This particular role of rev reflects a tight coupling of the splicing and nuclear export steps. In one embodiment, nucleic acid vector comprises an RRE sequence. In a further embodiment, the RRE sequence is derived from HIV-1 HXB2 sequence, which is available at Genome Accession No. K03455, for example from base pairs 7622 to 8479, or 7769 to 8146, in particular base pairs 7622 to 8479.

Rev binds to RRE and facilitates the export of singly spliced (env, vif, vpr and vpu) or non-spliced (gag, pol and genomic RNA) viral transcripts, thus leading to downstream events like gene translation and packaging (see Suhasini and Reddy (2009) *Curr. HIV Res.* 7(1): 91-100). In one embodiment, the nucleic acid vector additionally comprises the auxiliary gene rev or an analogous gene thereto (i.e. from other retroviruses or a functionally analogous system). Inclusion of the rev gene ensures efficient export of RNA transcripts of the retroviral vector genome from the nucleus to the cytoplasm, especially if an RRE element is also included on the transcript to be transported. In a further embodiment, the rev gene comprises at least 60% sequence identity, such as at least 70% sequence identity to base pairs 970 to 1320 of Genome Accession No. M11840 (i.e. HIV-1 clone 12 cDNA, the HIVPCV12 locus). In an alternative embodiment, the rev gene comprises at least 60% sequence identity, such as at least 70%, 80%, 90% or 100% sequence identity to base pairs 5970 to 6040 and 8379 to 8653 of Genome Accession No. K03455.1 (i.e. Human immunodeficiency virus type 1, HXB2).

Auxiliary genes are thought to play a role in retroviral replication and pathogenesis, therefore many current viral vector production systems do not include some of these genes. The exception is rev which is usually present or a system analogous to the rev/RRE system is potentially used. Therefore, in one embodiment, the nucleic acid sequences encoding one or more of the auxiliary genes vpr, vif, vpu, tat and nef, or analogous auxiliary genes, are disrupted such that said auxiliary genes are removed from the RNA genome of the retroviral vector particle or are incapable of encoding functional auxiliary proteins. In a further embodiment, at least two or more, three or more, four or more, or all of the auxiliary genes vpr, vit; vpu, tat and nef, or analogous auxiliary genes, are disrupted such that said auxiliary genes are removed from the RNA genome of the retroviral vector particle or are incapable of encoding functional auxiliary proteins. Removal of the functional auxiliary gene may not require removal of the whole gene; removal of a part of the gene or disruption of the gene will be sufficient.

It will be understood that the nucleic acid sequences encoding the replication defective retroviral vector particle may be the same as, or derived from, the wild-type genes of the retrovirus upon which the retroviral vector particle is based, i.e. the sequences may be genetically or otherwise altered versions of sequences contained in the wild-type virus. Therefore, the retroviral genes incorporated into the nucleic acid vectors or host cell genomes, may also refer to codon-optimised versions of the wild-type genes.

Gene Amplification

In nature, gene amplification is a process that characterises some normal developmental states, such as oogenesis in *Drosophila melanogaster*, particularly in the amplification of chorion genes in its ovaries (Spralding et al. (1980) *PNAS*, 77: 1096-1100). Gene amplification is also a frequent event in tumour cells, in which it plays a major role in oncogene activation by causing an enhancement of their expression (Albertson D. G. (2006) *Trends Genet.* 22: 447-455).

"Gene amplification" refers to a process by which specific DNA sequences of the genome (i.e. genes) are disproportionately replicated in relation to the other sequences in the genome such that the amplified DNA sequences becomes present in a higher copy number than was initially present in the genome before such disproportionate replication. "Amplified" or "amplification" as used herein with reference to a gene or nucleic acid sequence refers to a gene or nucleic acid sequence present in two or more copies in a host cell line by virtue of gene amplification.

The natural phenomenon of gene amplification has been exploited in the biopharmaceutical industry as a way of increasing the titre of a recombinant gene product produced by a cell line. Where a recombinant gene has been integrated into the host cell's genome, the copy number of the recombinant gene, and concomitantly the amount of recombinant protein expressed, can be increased by selecting for cell lines in which the recombinant gene has been amplified after integration into the host cell genome.

An "amplifiable selection marker gene" as used herein refers to a gene which permits the amplification of that gene under appropriate growth conditions. In contrast, the term "selectable marker gene" as used herein and as described in more detail below, refers to a selectable marker gene that does not permit amplification. The amplifiable selection marker gene is capable of responding either to an inhibitor or lack of an essential metabolite by amplification to increase the expression product (i.e. the expression of the protein encoded by the amplifiable selection marker gene). When an inhibitor, such as a toxic drug, is used, the increased expression of the amplifiable selection marker confers resistance against the inhibitor. In one embodiment, the amplifiable selection marker gene may be characterized as being able to complement an auxotrophic host. In one embodiment, the amplifiable selection marker is under the control of a promoter. In one embodiment, the promoter is an SV40 promoter.

The term "selectable marker gene" as used herein, refers to a gene that will help select cells actively expressing an inserted gene (e.g. nucleic acid vector) but that which does not permit amplification. Examples of suitable selection markers include, enzymes encoding resistance to an antibiotic (i.e. an antibiotic resistance gene), e.g., kanamycin, neomycin, puromycin, hygromycin, blasticidin, or zeocin. Another example of suitable selection markers are fluorescent proteins, for example green fluorescent protein (GFP), red fluorescent protein (RFP) or blue fluorescent protein (BFP).

An "amplifiable selection marker" and a "selectable marker" as used herein refers to the product (i.e. enzyme proteins) encoded for by the amplifiable selection marker gene and the selectabler marker gene, respectively.

Gene amplification may be induced by stably transfecting a host cell with an amplifiable selection marker gene. The stably transfected host cells are subjected to increasing concentrations of a toxic drug, which is known to inhibit the amplifiable selection marker. For example, the transfected cells may be cultured in a medium which contains the toxic drug at a concentration to achieve killing of greater than 98% of the cells within 3 to 5 days after plating the parent cells (i.e. non-transfected cells) in medium containing the toxic drug. Alternatively, the transfected cells may be cultured in a medium which contains the toxic drug (e.g. MTX or MSX) at 37° C. in a humidified atmosphere of 8% CO in air with shaking for 14 to 21 days or until viability of >90%. Through such inhibition, populations of cells can be selected that have increased expression levels of the amplifiable selection marker and, consequently, resistance to the drug at the concentration employed. Further methods for inducing gene amplification will be known to a person skilled in the art, such as that described in the OptiCHO™ Express Kit manual (Life Technologies™).

The nucleic acid vector of the present invention allows all of the expression constructs contained therein to be integrated at a single locus within the host cell genome. Amplification of the amplifiable selection marker gene also causes amplification of surrounding DNA sequences. As a result, the remaining DNA sequences of the nucleic acid vector which were integrated together into the host cell genome will also be amplified. In this way, by using the nucleic acid vector described herein, it is possible to provide a process for amplifying the retroviral vector genes stably integrated into a host cell genome, which is not reliant on in vivo ligation integration by the host cell of the multiple retroviral vector genes to the amplifiable selection marker gene.

Each amplifiable selection marker has an associated selection agent (i.e. a toxic drug), which is added to the cell culture media during amplification and selection regimes. Different amplifiable selection marker/selection agent combinations are known in the art, and any suitable amplification and selection regimes may be used in the present invention. Suitable amplifiable selection marker/selection agent combinations include adenosine deaminase/deoxycoformycin, aspartate transcarbannylase/N (phosphoacetyl)-L-aspartate, dihydrofolate reductase/methotrexate, glutamine synthetase/methionine sulphoximine and metallthionein-I/heavy metal.

In one embodiment, the amplifiable selection marker is dihydrofolate reductase (DHFR). The DHFR selection method involves incorporating an expression construct comprising the dhfr gene (i.e. amplifiable selection marker gene) to the nucleic acid vector thereby inducing a DHFR selection pressure to the other expression constructs of the nucleic acid vector. The host cell is transfected with the nucleic acid vector and grown in the presence of increasing concentrations of DHFR inhibitor methotrexate (MTX) to select for cells which have amplified the exogenous dhfr gene integrated into the host genome and concomitantly, the remaining integrated nucleic acid vector.

Expression constructs comprising the dhfr gene for use in gene amplification are well know in in the art and are described, for example, in Subramani et al. (1981) *Mol. Cell. Bio.* 2:854-864 and Walls et al. (1989) *Gene* 81:139-149.

In one embodiment the dhfr gene comprises at least 60% sequence identity, such as at least 70%, 80%, 90% or 100% sequence identity to Genome Accession No. NM_010049.3 In one embodiment, DHFR comprises at least 60% sequence identity, such as at least 70%, 80%, 90% or 100% sequence identity to Genome Accession No. NP_034179.

In one embodiment, the expression construct comprising nucleic acid sequences encoding DHFR may further comprise the components necessary for the transcription and translation of the polynucleotide from simian virus 40 genome.

In one embodiment, the expression construct comprising the nucleic acid sequences encoding an amplifiable selection marker is derived from pSV2-dhfras disclosed in Subramani et al. (1981) *Mol. Cell. Bio.* 2:854-864.

In a further embodiment, the nucleic acid sequence of the expression construct comprising a nucleic acid sequence encoding the amplifiable selection marker comprises the nucleic acid sequence of SEQ ID NO: 1. The nucleic acid sequence of SEQ ID NO: 1 is as set out in FIG. 2.

In another embodiment, the amplifiable selection marker is glutamine synthetase (GS). The GS selection method involves incorporating the gs gene to the nucleic acid vector, thereby inducing a GS selection pressure to the other expression constructs of the nucleic acid vector. The host cell is transfected with the nucleic acid vector and grown in the presence of increasing concentrations of GS inhibitor methionine sulfoximine (MSX) to select for cells which have amplified the gsgene integrated into the host genome and concomitantly, the remaining integrated nucleic acid vector.

Expression constructs comprising the gs gene for use in gene amplification are well know in in the art and are described, for example, in WO874462 and Bebbington et al. (1992) *Nature* 10:169-175).

By using the amplifiable selection marker and associated selection agent in this way, the area of the host cell genome harbouring the selection pressure can amplify, thereby increasing the copy number of the amplifiable selection marker and the nucleic acid vector. The cell lines that are grown through such rounds of amplification and selection are then screened for the titre of the retroviral vector production and the best clone is selected for use in mass production.

Typically, both the number of rounds of amplification and the concentration of the associated agent employed are not set or fixed. Instead, it is typical for amplification and selection regimes to become progressively stringent up to a point in which a production threshold is reached. It has been observed that up until a "plateau" of protein production is approached, the levels of protein production observed are typically proportionate to the increase in gene copy number (Bebbington and Hentschel, *DNA Cloning Volume III*, IRL press, 1987).

In a preferred embodiment, the host cell is negative for the amplifiable selection marker. That is to say, that the host cell does not comprise an endogenous amplifiable selection marker gene. For example, when using DHFR as the amplifiable selection marker, it is preferable to employ DHFR-negative host strains, such as CHO DG44 or CHO DUX-B11. In one embodiment, the host cell is a GS-negative host strain. In one embodiment, the host cell is modified to knock out the endogenous gs gene. Methods for knocking out specific genes of a cell are well known in the art, for example, using zinc finger nucleases. In a preferred embodiment, the host cell is a GS negative HEK293T cell. However, the invention is not limited by the choice of a particular host cell line. Any cell line which has a rapid rate of growth (e.g., a doubling time of 12 hours or less) and which is capable of amplifying the exogenous amplifiable selection marker gene at a reasonable rate without amplification of the endogenous amplifiable selection marker gene at a similar or higher rate, such that the exogenous amplifiable selection marker can be used as a dominant marker, may be used in the methods of the present invention.

Cell lines transduced with the dominant marker (i.e. exogenous amplifiable selection marker) are identified by determining that the ability of the cell to grow in increasing concentrations of the selection agent correlates with an increase in the copy number of the amplifiable selection marker (this may be measured directly by demonstrating an increase in the copy number of the amplifiable marker by Southern blotting or indirectly by demonstrating an increase in the amount of mRNA produced from the amplifiable marker by Northern blotting, or qPCR).

Where a host cell comprises an endogenous amplifiable selection marker gene, the nucleic acid vector may further comprise a nucleic acid sequence encoding a selectable marker in addition to the amplifiable selection marker. The host cells are transfected with a nucleic acid vector comprising an amplifiable selection marker as well as a selectable marker. Where the selectable marker confers antibiotic resistance, the transfected host cells are first selected for the ability to grow in the presence of the respective antibiotic, such as zeocin or hygromycin. In this way, it is possible to select for host cells which have been successfully transfected with nucleic acid vector, prior to inducing gene amplification. The cells are then selected for the ability to grown in increasing concentrations of the selection agent, such as MTX or MSX.

Therefore, in one embodiment, the nucleic acid vector additionally comprises a selectable marker gene. In a further embodiment, the selectable marker gene is an antibiotic resistance gene, such as a zeocin, kanamycin or puromycin resistance gene, in particular a zeocin (ZeoR) resistance gene. In a yet further embodiment, the zeocin resistance gene is derived from the *Streptoalloteichus hindustans* ble gene, for example see Genome Accession No. X52869.1 from base pairs 3 to 377. In another embodiment, the selectable marker is hygromycin phosphotransferase.

Additional Components

The nucleic acid vectors of the invention may comprise further additional components. These additional features may be used, for example, to help stabilize transcripts for translation, increase the level of gene expression, and turn on/off gene transcription.

The retroviral vector particles produced by the invention may be used in methods of gene therapy. Therefore, in one embodiment, the nucleic acid vector additionally comprises one or more transgenes. For example, when a target gene is not expressed correctly in the mammalian host cell, therefore a corrected version of the target gene is introduced as the transgene. In other words, the transgene is a therapeutically active gene which encodes a gene product which may be used to treat or ameliorate a target disease. The transgene may encode, for example, an antisense RNA, a ribozyme, a protein (for example a tumour suppressor protein), a toxin, an antigen (which may be used to induce antibodies or helper T-cells or cytotoxic T-cells) or an antibody (such as a single chain antibody). The transgene can encode any polypeptide or RNA that is desirably produced in a cell in vitro, ex vivo, or in vivo. In one embodiment, the transgene encodes beta globin. The transgene may have been obtained from another cell type, or another species, or prepared synthetically. Alternatively, the transgene may have been obtained from the host cell, but operably linked to regulatory regions which are different to those present in the native gene. Alternatively, the transgene may be a different allele or variant of a gene present in the host cell.

Multiple copies of the transfer vector containing the transgene are expected to result in higher retroviral vector titre, therefore, in one embodiment, the nucleic acid vector comprises multiple copies of the transgene, such as two or more, in particular three or more, copies of the transgene. In some cases more than one gene product is required to treat a disease, therefore in a further embodiment, the nucleic acid vector additionally comprises two or more, such as three or more, or four or more, different transgenes.

The aim of gene therapy is to modify the genetic material of living cells for therapeutic purposes, and it involves the insertion of a functional gene into a cell to achieve a therapeutic effect. The retroviral vector produced using the nucleic acid vectors and host cells described herein can be used to transfect target cells and induce the expression of the gene of potential therapeutic interest. The retroviral vector can therefore be used for treatment of a mammalian subject, such as a human subject, suffering from a condition including but not limited to, inherited disorders, cancer, and certain viral infections.

It will be understood by those skilled in the art that the nucleic acid sequences can be operably associated with appropriate control sequences. For example, the nucleic acid sequences can be operably associated with expression control elements, such as transcription/translation control signals, origins of replication, polyadenylation signals, internal ribosome entry sites (IRES), promoters, and/or enhancers, and the like.

In one embodiment, the nucleic acid vector additionally comprises a transcription regulation element. For example, any of the elements described herein may be operably linked to a promoter so that expression can be controlled. Promoters referred to herein may include known promoters, in whole or in part, which may be constitutively acting or inducible, e.g. in the presence of a regulatory protein. In one embodiment, the promoter is a viral promoter. In one embodiment, the nucleic acid vector additionally comprises a high efficiency promoter, such as a CMV promoter. This promoter has the advantage of promoting a high level of expression of the elements encoded on the non-mammalian nucleic acid vector. In a further embodiment, the CMV promoter comprises a sequence derived from the human cytomegalovirus strain AD169. This sequence is available at Genome Accession No. X17403, for example from base pairs 173731 to 174404. In an alternative embodiment the promoter is a SV40 late promoter from simian virus 40. Promoters referred to herein may include known promoters, in whole or in part, which may be constitutively acting or inducible, e.g. in the presence of a regulatory protein.

In one embodiment, the promoter (such as a CMV promoter) additionally comprises at least one Tet operon. The Tet operon system may be used to control expression of the retroviral sequences contained within the nucleic acid vector. Briefly, the Tet repressor protein blocks expression by binding to the Tet operon site which is introduced into the promoter. Therefore, when the Tet repressor is bound to the Tet operon, there is no gene expression. On addition of tetracycline or doxycyclin, the Tet repressor is sequestered allowing promoter activity, therefore gene expression is switched on. Tet operon systems are widely available, such as the Tet operon used in the pcDNA™4/TO mammalian expression vector available from Invitrogen.

In one embodiment, the nucleic acid vector additionally comprises a tetracycline resistance operon repressor protein ("Tet repressor" or "TetR"). In a further embodiment, the Tet repressor is codon optimised.

In one embodiment, the nucleic acid vector additionally comprises an insulator, such as a chromatin insulator. The term "insulator" refers to a genetic sequence which blocks the interaction between promoters and enhancers. In a further embodiment, the insulator (such as a chromatin insulator) is present between each of the retroviral nucleic acid sequences (i.e. between individual expression constructs). This helps to prevent promoter interference (i.e. where the promoter from one transcription unit impairs expression of an adjacent transcription unit) between adjacent retroviral nucleic acid sequences. Without being bound by theory, this is also thought to help minimise the risk of recombination between retroviral sequences to generate replication-competent virus.

It will be understood that if the insulators are present in the nucleic acid vector between each of the retroviral nucleic acid sequences, then these may be arranged as individual expression constructs within the nucleic acid vector. For example, each sequence encoding the retroviral nucleic acid sequences has its own promoter and/or an intron and/or polyA signal.

In one embodiment, the chromatin insulator has at least 90% sequence identity, for example at least 95% sequence identity, to the chicken (*Gallus gallus*) HS4 insulator sequence (for example see Genome Accession No. U78775.2, base pairs 1 to 1205).

In one embodiment, the nucleic acid vector additionally comprises a polyA signal. The use of a polyA signal has the advantage of protecting mRNA from enzymatic degradation and aiding in translation. In a further embodiment, the polyA signal is obtained from or derived from SV40, Bovine Growth Hormone and/or Human Beta Globin. In one embodiment, the polyA signal is derived from the SV40 early polyA signal (for example, see Genome Accession No. EF579804.1, base pairs 2668 to 2538 from the minus strand). In one embodiment, the polyA signal is derived from the Human Beta Globin polyA signal (for example, see Genome Accession No. GU324922.1, base pairs 3394 to 4162).

In one embodiment, the nucleic acid vector additionally comprises an intron sequence. The use of an intron downstream of the enhancer/promoter region and upstream of the cDNA insert (i.e. the transgene) is known to increase the level of expression of the insert. In a further embodiment, the intron sequence is a Human Beta Globin Intron or the Rabbit Beta Globin Intron II sequence. In one embodiment, the Human Beta Globin Intron is derived from the sequence available at Genome Accession No. KM504957.1 (for example from base pairs 476 to 1393). In one embodiment, the Rabbit Beta Globin Intron II is derived from the sequence available at Genome Accession No. V00882.1 (for example, from base pairs 718 to 1290).

In one embodiment, the nucleic acid vector additionally comprises a woodchuck hepatitis virus post-transcriptional regulatory element (WPRE). The presence of WPRE has been shown to enhance expression and as such is likely to be beneficial in attaining high levels of expression. In a further embodiment, the WPRE is derived from the sequence available at Genome Accession No. J04514.1 (for example, from base pairs 1093 to 1684).

In one embodiment, the nucleic acid vector additionally comprises an internal ribosome entry site (IRES). An IRES is a structured RNA element that is usually found in the 5'-untranslated region downstream of the 5'-cap (which is required for the assembly of the initiation complex). The IRES is recognized by translation initiation factors, and allows for cap-independent translation. In a further embodiment, the IRES is derived from the Encephalomyocarditis virus (EMCV) genome (for example, see Genome Accession No. KF836387.1, base pairs 151 to 724).

In one embodiment, the nucleic acid vector additionally comprises a Multiple Cloning Site (MCS). An MCS is a short segment of DNA within the nucleic acid vector which contains multiple restriction sites (for example, 10, 15 or 20 sites). These sites usually occur only once within the nucleic acid vector to ensure that the endonuclease only cuts at one site. This allows for the retroviral genes to be easily inserted using the appropriate endonucleases (i.e. restriction enzymes).

It will be understood by a person skilled in the art that the constructs may be arranged in any order within the nucleic acid vector. In an exemplary embodiment, the nucleic acid vector comprises the following insert: a nucleic acid sequence encoding an amplifiable selection marker, a retroviral nucleic acid sequence encoding the gag and pol proteins, a retroviral nucleic acid sequence encoding the env protein or a functional substitute thereof (such as VSVg), a retroviral nucleic acid sequence encoding the auxiliary gene rev (such as a codon optimised rev sequence) or an analogous gene thereto or a functionally analogous system, a tetracycline resistance operon repressor protein (TetR), an internal ribosome entry site, and a selectable marker (such as a zeocin resistance selection marker) (i.e., Amplifiable selection marker-GagPol-Env-Rev-TetRepressor-IRES-Antibiotic Resistance marker-remaining BAC sequence ("BAC bone"); or Amplifiable selection marker-GagPol-(wild-type) VSVg-(codon-optimized)-Rev-TetRepressor-IRES-Zeocin-Resistance-pSMARTBAC). In a further embodiment, an insulator (such as a chromatin insulator) is present between each of the amplifiable selection marker, gagpol, env, and rev sequences. In a further embodiment, a promoter is present before each of the amplifiable selection marker, gagpol, env and rev sequences. In a yet further embodiment, at least one copy of the transfer vector sequence (i.e. comprising nucleic acid sequences which encode the RNA genome of a retroviral vector particle) is present before the amplifiable selection marker sequence.

In one embodiment, the nucleic acid vector comprises the following insert: a promoter (such as a CMV promoter optionally comprising a Tet operon sequence), an intron (such as a human beta globin intron), nucleic acid sequence encoding an amplifiable selection marker, a polyA signal (such as a human beta globin polyA signal), an insulator (such as a chromatin insulator), a promoter (such as a CMV promoter optionally comprising a Tet operon sequence), an intron (such as a human beta globin intron), a retroviral nucleic acid sequence encoding the gag and pol proteins, a retroviral nucleic acid encoding RRE, a polyA signal (such as a human beta globin polyA signal), an insulator (such as a chromatin insulator), a promoter (such as a CMV promoter optionally comprising a Tet operon sequence), an intron (such as a human beta globin intron), a retroviral nucleic acid sequence encoding the env protein or a functional substitute thereof (such as VSVg), a polyA signal (such as a human beta globin polyA signal), an insulator (such as a chromatin insulator), a promoter (such as a CMV promoter optionally comprising a Tet operon sequence), a retroviral nucleic acid sequence encoding the auxiliary gene rev or an analogous gene thereto or a functionally analogous system, a polyA signal (such as a human beta globin polyA signal), an insulator (such as a chromatin insulator), a promoter (such as a CMV promoter), an intron (such as a rabbit beta globin intron), a tetracycline resistance operon repressor protein (TetR), an internal ribosome entry site, a selectable marker (such as a zeocin resistance selection marker), a polyA signal and a multiple cloning site.

The nucleic acid sequences may be introduced into the nucleic acid vector sequentially. This allows for selection after each integration to ensure that all of the required nucleic acid sequences are successfully integrated into the nucleic acid vector. Alternatively, at least two or more of the nucleic acid sequences are introduced into the nucleic acid vector simultaneously.

It will be understood that the additional genes described herein may be introduced into the nucleic acid vector by standard molecular cloning techniques known in the art, for example using restriction endonucleases and ligation techniques. Furthermore, the nucleic acid vector, in particular BACs, PACs, fosmids and/or cosmids, may be introduced into bacterial host cells (such as E. coli cells, in particular the E. coli strain DH10B) by standard techniques, such as electroporation.

Uses

According to a further aspect of the invention, there is provided the nucleic acid vector defined herein for use in producing a retroviral packaging or producer cell line.

The nucleic acid vectors described herein may be used to create a retroviral packaging cell line which would greatly simplify retroviral vector production. It will be understood that if nucleic acid sequences encoding the RNA genome of the retroviral vector (comprising the transgene) is included on the nucleic acid vector, then this would be used to create a producer cell line.

As described herein, it would be useful to develop a stable retroviral packaging or producer cell line in order to overcome the difficulties associated with transient transfection and reduced retroviral vector particle titres. The nucleic acid vectors described herein can be used to prepare said packaging or producer cell lines because they are able to hold large DNA inserts containing the essential genes required for retroviral packaging which can then be integrated into the endogenous genome of mammalian host cells in one step and amplified as a unit such that the amplification and subsequent expression of the essential retroviral genes are proportional relative to each other.

Host Cells

According to a further aspect of the invention, there is provided a retroviral packaging cell comprising nucleic acid sequences encoding:

gag and pol proteins;
env protein or a functional substitute thereof; and
an amplifiable selection marker;
as individual expression constructs, wherein said expression constructs are all integrated together at a single locus within the retroviral packaging cell genome as a unit; and
wherein the copy number of the unit is two or more.

The advantage of including all of the retroviral genes and the amplifiable selection marker on a large nucleic acid vector is that they can be prepared in microbial cells (such as bacterial or yeast cells) first, which are much easier to handle and manipulate, before being integrated into mammalian cells in a single step. This relieves selection pressure and reduces the silencing timeframe once the retroviral genes have been integrated into a mammalian host cell. The characteristic feature of this method is that all of the retroviral genes required to create a packaging cell line are present in a single locus in the endogenous genome as a unit, rather than randomly scattered throughout the endogenous genome. This has the advantage of producing a retroviral packaging cell which expresses all of the retroviral genes at the same level because they are integrated at the same locus, as compared to previously known methods in which the retroviral genes are integrated separately and randomly throughout the host cell's genome which may cause uneven levels of expression.

Furthermore, by having the amplifiable selection marker on the same nucleic acid vector as all of the expression constructs comprising nucleic acid sequences encoding the essential retroviral protein (gag, pol, env or a functional substitute thereof), the expression constructs are amplified together.

It will be understood that the unit may integrate more than once in the host cell genome at multiple different locations on different chromosomes (albeit with all of the encoded nucleic acid sequences present in a single locus). Therefore, reference to a "single locus" does not exclude the possibility that the nucleic acid sequences are all integrated together at multiple loci within the retroviral packaging/producer cell genome. This may be beneficial for increasing expression levels of the transgenes and could potentially improve retroviral titres. It is possible to compare the copy number of construct insertions between cell populations derived from individual clones by qPCR.

In one embodiment, the retroviral packaging cell additionally comprises nucleic acid sequences which encode the RNA genome of the retroviral vector particle. Such nucleic acid sequences may also be integrated at the single locus with the nucleic acid sequences encoding the gag and pol proteins, the env protein or a functional substitute thereof and the amplifiable selection marker. Therefore, according to a further aspect of the invention, there is provided a retroviral producer cell comprising nucleic acid sequences encoding:

gag and pol proteins;
env protein or a functional substitute thereof;
an amplifiable selection marker; and
an RNA genome of a retroviral vector particle
as individual expression constructs, wherein said expression constructs are all integrated together at a single locus within the retroviral producer cell genome as a unit; and
wherein the copy number of the unit is two or more.

In one embodiment, the retroviral packaging cell is a mammalian cell. In a further embodiment, the mammalian cell is selected from a HEK 293 cell, CHO cell, Jurkat cell, KS62 cell, PerC6 cell, HeLa cell or a derivative or functional equivalent thereof. In one embodiment the mammalian cell is CHO-K1 or CHO-K1SV. In a yet further embodiment, the mammalian host cell is a HEK 293 cell, or derived from a HEK 293 cell. Such cells could be adherent cell lines (i.e. they grow in a single layer attached to a surface) or suspension adapted/non-adherent cell lines (i.e. they grow in suspension in a culture medium). Cells that grow in suspension are extensively used in industry for the production of biological products as they grow to great densities, and production is easy to scale-up as compared to adherent cells. In a yet further embodiment, the HEK 293 cell is a HEK 293T cell. The term "HEK 293 cell" refers to the Human Embryonic Kidney 293 cell line which is commonly used in biotechnology. In particular, HEK 293T cells are commonly used for the production of various retroviral vectors. Other examples of suitable commercially available cell lines include T-REX™ (Life Technologies) cell lines. Preferably, the mammalian cell does not express the amplifiable selection marker endogenously. For example, where the amplifiable selection marker is DHFR, it is preferable to employ a dhfr (dhfr negative) cell line, such as a dhfr CHO cell line, or where the amplifiable selection marker is GS, it is preferable to employ a gs (gs negative) cell line, for example, a HEK293 cell line modified to knock out with the gs gene to produce GS negative HEK293T. Methods for knocking out specific genes of a cell are well known in the art, for example, using zinc finger nucleases.

In a preferred embodiment, the host cell is negative for the amplifiable selection marker. That is to say, that the host cell genome does not comprise an endogenous amplifiable selection marker gene. For example, when using DHFR as the amplifiable selection marker, it is preferable to employ DHFR-negative host strains, such as CHO DG44 or CHO DUX-B11. In one embodiment, the host cell is a GS-negative host strain. In one embodiment, the host cell is modified to knock out the endogenous gs gene. In a preferred embodiment, the host cell is a GS negative HEK293T cell. However, the invention is not limited by the choice of a particular host cell line. Any cell line which has a rapid rate of growth (i.e. a doubling time of 12 hours or less) and which is capable of amplifying the amplifiable selection marker gene at a reasonable rate without amplification of the endogenous amplifiable selection marker gene at a similar or higher rate may be used in the methods of the present invention. Cell lines which have the ability to amplify the amplifiable selection marker gene at a rate which is greater than the rate at which the endogenous selection marker gene is amplified are identified by finding that the ability of the cell to grow in increasing concentrations of the selection agent (i.e. the compound which requires the cell to express the amplifiable selection marker in order to survive) correlates with an increase in the copy number of the amplifiable selection marker (this may be measured directly by demonstrating an increase in the copy number of the amplifiable marker by Southern blotting or indirectly by demonstrating an increase in the amount of mRNA produced from the amplifiable marker by Northern blotting).

It will be understood that all of the embodiments described hereinbefore for the nucleic acid vector, may also be applied to the retroviral packaging/producer cells of the invention.

Methods

According to a further aspect of the invention, there is provided a method of producing a stable retroviral packaging or producer cell line, comprising the steps of:
  (a) transfecting the nucleic acid vector described herein into a culture of mammalian host cells;
  (b) growing the transfected mammalian host cells in a medium which contains a concentration of a selection agent that inhibits the growth of the transfected mammalian cells which express insufficient levels of the amplifiable selection marker; and
  (c) selecting transfected mammalian host cells capable of growth in said medium, wherein the selected transfected mammalian host cells contain an amplified number of copies of the nucleic acid vector integrated into the transfected mammalian host cell genome.

Whether a producer or packaging cell line is produced is dependent on whether the nucleic acid vector comprises or does not comprise nucleic acid sequence encoding the RNA genome of the retroviral vector particle, respectively.

If the target genes are integrated into the endogenous chromosomes with a selectable marker, such as an antibiotic resistance gene, then the method may additionally comprise selecting for the mammalian host cells in which the retroviral nucleic acids have successfully integrated. Therefore, in one embodiment, the method comprises a further step, after step a), of selecting within the culture for a mammalian host cell which has the nucleic acid sequences encoded on the vector integrated into an endogenous chromosome of the mammalian host cell.

The stably transfected host cells are subjected to increasing concentrations of a selection agent (e.g. toxic drug), which is known to inhibit the amplifiable selection marker. For example, the transfected cells may be cultured in a medium which contains the toxic drug at a concentration to achieve killing of greater than 98% of the cells within 3 to 5 days after plating the parent cells (i.e. non-transfected cells) in medium containing the toxic drug. Alternatively, the transfected cells may be cultured in a medium which contains the toxic drug (e.g. MTX or MSX) at 37° C. in a humidified atmosphere of 8% CO in air with shaking for 14 to 21 days or until viability of >90%. Through such inhibition, populations of cells can be selected that have increased expression levels of the amplifiable selection marker and, consequently, resistance to the drug at the concentration employed. Steps b) and c) may be repeated with progressively increasing concentrations of the selection agent. In one embodiment amplification of the exogenous genes is achieved by selection for resistance to progressively increased levels of a selection agent by repeating steps b) and c).

Methods for inducing gene amplification will be known to a person skilled in the art, such as that described in the OptiCHO™ Express Kit manual (Life Technologies™).

In one embodiment, the mammalian host cell is selected from a HEK 293 cell, HEK 6E cell, CHO cell, Jurkat cell, KS62 cell, PerC6 cell, HeLa cell or a derivative or functional equivalent thereof. In a further embodiment, the mammalian host cell is a HEK 293 cell, or derived from a HEK 293 cell. Such cells could be adherent cell lines (i.e. they grow in a single layer attached to a surface) or suspension adapted/non-adherent cell lines (i.e. they grow in suspension in a culture medium). In a yet further embodiment, the HEK 293 cell is a HEK 293T cell or HEK 6E cell. Other examples of suitable commercially available cell lines include T-REX™ (Life Technologies) cell lines.

In a preferred embodiment, the host cell is negative for the amplifiable selection marker. That is to say, that the host cell genome does not comprise an endogenous amplifiable selection marker gene. For example, when using DHFR as the amplifiable selection marker, it is preferable to employ DHFR-negative host strains, such as CHO DG44 or CHO DUX-B11. In one embodiment, the host cell is a GS-negative host strain. In one embodiment, the host cell is modified to knock out the endogenous gs gene. Methods for knocking out specific genes of a cell are well known in the art, for example, using zinc finger nucleases. In a preferred embodiment, the host cell is a GS negative HEK293T cell.

However, the invention is not limited by the choice of a particular host cell line. Any cell line which has a rapid rate of growth (i.e., a doubling time of 12 hours or less) and which is capable of amplifying the amplifiable selection marker gene at a reasonable rate without amplification of the endogenous amplifiable selection marker gene at a similar or higher rate may be used in the methods of the present invention. Cell lines which have the ability to amplify the amplifiable selection marker gene at a rate which is greater than the rate at which the endogenous selection marker gene is amplified are identified by finding that the ability of the cell to grow in increasing concentrations of the selection agent (i.e. the compound which requires the cell to express the amplifiable selection marker in order to survive) correlates with an increase in the copy number of the amplifiable selection marker (this may be measured directly by demonstrating an increase in the copy number of the amplifiable marker by Southern blotting or indirectly by demonstrating an increase in the amount of mRNA produced from the amplifiable marker by Northern blotting).

The skilled person will be aware that introducing the nucleic acid vector into the host cell may be performed using suitable methods known in the art, for example, lipid-mediated transfection, microinjection, cell (such as microcell) fusion, electroporation or microprojectile bombardment. In one embodiment, the nucleic acid vector is introduced into the host cell by electroporation. It will be understood that the choice of method to use for introducing the nucleic acid vector can be chosen depending upon the type of mammalian host cell used.

Once inside the mammalian host cell, the nucleic acid vector will randomly integrate into the endogenous genome of the mammalian host cell. Therefore, the method additionally comprises selecting for the mammalian host cell in which the nucleic acids encoded on the nucleic acid vector have integrated (for example, using an antibiotic resistance selection marker, such as a zeocin resistance marker).

The skilled person will be aware of methods to encourage integration of the nucleic acid vector, for example, linearising the nucleic acid vector if it is naturally circular (for example, BACs, PACs, cosmids or fosmids). The nucleic acid vector may additionally comprise areas of shared homology with the endogenous chromosomes of the mammalian host cell to guide integration to a selected site within the endogenous genome. Furthermore, if recombination sites are present on the nucleic acid vector then these can be used for targeted recombination. For example, the nucleic acid vector may contain a loxP site which allows for targeted integration when combined with Cre recombinase (i.e. using the Cre/lox system derived from P1 bacteriophage). Alternatively (or additionally), the recombination site is an alt site (e.g. from lambda phage), wherein the att site permits site-directed integration in the presence of a lambda integrase. This would allow the retroviral genes to be targeted to a locus within the endogenous genome which allows for high and/or stable expression.

Other methods of targeted integration are well known in the art. For example, methods of inducing targeted cleavage of genomic DNA can be used to encourage targeted recombination at a selected chromosomal locus. These methods often involve the use of engineered cleavage systems to induce a double strand break (DSB) or a nick in the endogenous genome to induce repair of the break by natural processes such as non-homologous end joining (NHEJ) or repair using a repair template (i.e., homology directed repair or HDR).

Cleavage can occur through the use of specific nucleases such as engineered zinc finger nucleases (ZFN), transcription-activator like effector nucleases (TALENs), using the CRISPR/Cas9 system with an engineered crRNA/tracr RNA ('single guide RNA') to guide specific cleavage, and/or using nucleases based on the Argonaute system (e.g., from T. thermophilus, known as 'TtAgo', see Swarts et al. (2014) Nature 507(7491): 258-261). Targeted cleavage using one of these nuclease systems can be exploited to insert a nucleic acid into a specific target location using either HDR or NHEJ-mediated processes. Therefore, in one embodiment, the method additionally comprises integrating the nucleic acid sequences encoded on the nucleic acid vector into the genome (i.e. an endogenous chromosome) of the mammalian host cell using at least one nuclease, wherein the at least one nuclease cleaves the genome of the mammalian host cell such that the nucleic acid sequences are integrated into the genome of the cell. In a further embodiment, the at least one nuclease is selected from the group consisting of a zinc finger nuclease (ZFN), a TALE nuclease (TALEN), a CRISPR/Cas nuclease system and combinations thereof.

According to a further aspect of the invention, there is provided a retroviral packaging or producer cell obtained by the method defined herein.

The cell line obtained using the methods defined herein may be used to produce a cell line with improved titre of retroviral vector particle.

References herein to the term "titre" refer to an effective amount of retroviral vector or particle which is capable of transducing a target cell, such as a patient cell. In one embodiment, a high titre is in excess of $10^6$ TU/ml without concentration (TU=transducing units).

According to a further aspect of the invention, there is provided a method of producing a replication defective retroviral vector particle, comprising the steps of:

(a) transfecting the nucleic acid vector described herein into a culture of mammalian host cells;

(b) growing the transfected mammalian host cells in a medium which contains a concentration of a selection agent that inhibits the growth of the transfected mammalian host cells which express insufficient levels of the amplifiable selection marker;

(c) selecting transfected mammalian host cells capable of growth in said medium, wherein the selected transfected mammalian host cells contain an amplified number of copies of the nucleic acid vector integrated into the transfected mammalian host cell genome; and (d) further culturing the mammalian host cells selected in step (c) under conditions in which the replication defective retroviral vector particle is produced.

Steps b) and c) may be repeated with progressively increasing concentrations of the selection agent. Therefore, in one embodiment amplification of the exogenous genes is achieved by selection for resistance to progressively increased levels of a selection agent by repeating steps b) and c).

If the target genes are integrated into the endogenous chromosomes with a selectable marker, such as an antibiotic resistance gene, then the method may additionally comprise selecting for the mammalian host cells in which the retroviral nucleic acids have successfully integrated. Therefore, in one embodiment, the method comprises a further step, after step a), of selecting within the culture for a mammalian host cell which has the nucleic acid sequences encoded on the vector integrated into an endogenous chromosome of the mammalian host cell.

As described hereinbefore, in one embodiment, the mammalian host cell is selected from a HEK 293 cell, CHO cell, Jurkat cell, KS62 cell, PerC6 cell, HeLa cell or a derivative or functional equivalent thereof. In a further embodiment, the mammalian host cell is a HEK 293 cell, or derived from a HEK 293 cell. Such cells could be adherent cell lines (i.e. they grow in a single layer attached to a surface) or suspension adapted/non-adherent cell lines (i.e. they grow in suspension in a culture medium). In a yet further embodiment, the HEK 293 cell is a HEK 293T cell. Other examples of suitable commercially available cell lines include T REX™ (Life Technologies) cell lines.

In a preferred embodiment, the host cell is negative for the amplifiable selection marker. That is to say, that the host cell genome does not comprise an endogenous amplifiable selection marker gene. For example, when using DHFR as the amplifiable selection marker, it is preferable to employ DHFR-negative host strains, such as CHO DG44 or CHO DUX-B11. In one embodiment, the host cell is a GS-negative host strain. In one embodiment, the host cell is modified to knock out the endogenous gs gene. Methods for knocking out specific genes of a cell are well known in the art, for example, using zinc finger nucleases. In a preferred embodiment, the host cell is a GS negative HEK293T cell. However, the invention is not limited by the choice of a particular host cell line.

It will be understood by the skilled person that the conditions used in the method described herein will be dependent upon the host cell used. Typical conditions, for example the culture medium or temperature to be used, are well known in the art. In one embodiment, culturing is performed by incubating the mammalian host cell under humidified conditions. In a further embodiment, the humidified conditions comprise incubating the transfected cells at 37° C. at 5% $CO_2$. In one embodiment, culturing is performed using a culture medium selected from: Dulbecco's modified Eagle's medium (DMEM) containing 10% (vol/vol) fetal bovine serum (FBS), serum-free UltraCULTURE™ medium (Lonza, Cat. No. 12-725F), BalanCD HEK293® medium (Irvine Scientific Cat No 911615) or FreeStyle™ Expression medium (Thermo fisher, Cat. No. 12338-018).

Appropriate culturing methods are well known to a person skilled in the art. For example, the cell may be cultured in suspension and/or in animal component-free conditions. In one embodiment, the cell is suitable for culturing in any volume of culture medium, from 10 ml (e.g. in shaker flasks) to 10 L, 50 L, 100 L, or more (e.g. in bioreactors).

In one embodiment, the method additionally comprises isolating the replication defective retroviral vector particle. For example, in one embodiment the isolating is performed by using a filter. In a further embodiment, the filter is a low-protein binding membrane (e.g. a 0.22 µm low-protein binding membrane or a 0.45 µm low-protein binding membrane), such as polyvinylidene fluoride (PVDF) or polyethersulfone (PES) artificial membranes.

Once inside the mammalian host cell, the retroviral nucleic acids present on the nucleic acid vector may integrate into a random, single locus within the endogenous genome. The integration step may be encouraged as described hereinbefore, for example using linearisation and/or areas of shared homology. Recombination sites may also be used for targeted recombination.

Once isolated, the retroviral vector particles may be concentrated for in vivo applications. Concentration methods include, for example, ultracentrifugation, precipitation or anion exchange chromatography. Ultracentrifugation is useful as a rapid method for retroviral vector concentration at a small scale. Alternatively, anion exchange chromatography (for example using Mustang Q anion exchange membrane cartridges) or precipitation (for example using PEG 6000) are particularly useful for processing large volumes of lentiviral vector supernatants.

According to a further aspect of the invention, there is provided a replication defective retroviral vector particle obtained by the method defined herein.

The invention will now be described in further detail with reference to the following, non-limiting Examples.

EXAMPLES

Example 1: Construct Guide (BAC)

FIG. 1 shows a stepwise guide to the construction of BACpack-WTGP-277delU5 and BACpack-SYNGP-277delU5. Owing to the compatible ends of an XbaI and NheI digest, the lentiviral packaging genes were progressively loaded into the pSmart BAC vector. At the point of GagPol addition, 2 constructs were made containing either Wild type GagPol (WTGP) or the codon optimised GagPol, SYNGP. These were given the nomenclature of BACpack-WTGP and of BACpack-SYNGP respectively. The transfer cassette was then loaded onto both of these constructs and so generating BACpackWTGP-277delU5 and BACpackSYNGP-277delU5.

Example 2: Selection of a Stable Polyclonal Pool

Polyclonal stable transfectant pools were generated by transfecting the adherent cell line, HEK293T, with BACpackSYNGP-277delU5 or BACpackWTGP-277delU5. Successful integration events were then selected for with Zeocin.

To assess the ability of these polyclonal pools to generate lentiviral vector, the cells were induced with Doxycycline (I) or left un-induced (UI) and compared to untransfected HEK293T cells.

The results show the titre in transduction units (TU)/mL, of the lentiviral vector supernatant harvested from each transfection condition. It can be seen from the titration results in FIG. 2 that the stable polyclonal pools, generated with either BACpackSYNGP-277delU5 or BACpack-WTGP-277delU5 are capable of producing lentiviral vector at concentrations in region of 10e7 TU/mL which is comparable to the current transient transfection system.

The results confirm that the single BAC vector containing all of the packaging genes necessary for lentiviral production can generate cell lines capable of producing lentiviral vector at suitable titre.

Example 3: Generating Stable Transfection Suspension Clones

The primary purpose of generating lentiviral vector producing cell lines using the BAC technology is to rapidly apply new advances to the platform. These advances are likely to include modification of specialist cell lines. For example, it is an industry standard to increase yield by producing biological products in suspension cells as they grow to greater densities than adherent cells. However, the current lentiviral vector production system relies on high transfection rates which are harder to achieve in suspension cells than adherent HEK293T cells. As transfection efficiency is less of a concern when generating a stable cell line due to the selection of successful integrants, the BAC construct is an ideal solution to generate lentiviral vector producing suspension cell lines.

As previously demonstrated, the BAC construct is capable of generating lentiviral vector producer cell lines from adherent HEK293T cells. To prove the flexibility of the BAC constructs, stable transfectant cell lines were generated from the suspension cell line HEK293 6E. The HEK293 6E cells were transfected with the BAC construct BACpack-WTGP-277delU5 then selected with Zeocin. This was followed by cloning to generate clonal cell lines. The results in FIG. 3 show the GFP signal generated by the stable cell lines. This indicates both the presence of Zeocin resistance and a functional GFP expression cassette in the transfer vector segment.

This result suggests that the BAC construct is capable of generating stable clones from multiple cell lines.

Example 4: Induction of Lentivirus in the Suspension Clones

In order to confirm the ability of the stable suspension clones to produce lentiviral vector, clones 1, 14, 15 and 16, were induced with 2 µg/ml doxycycline and the supernatant measured for viral titre by transduction of HEK293T cells.

The results in FIG. 4 show the titre in transduction units (TU)/mL, of the lentiviral vector supernatant harvested from each clone. The results clearly show that cell lines generated by stable transfection of the suspension cell line HEK293 6E with BACpackWTGP-277delU5 are capable of producing lentiviral vector at yields comparable to the current transient transfection system.

Example 5: Vector Titre of Clones

Figure 5A:
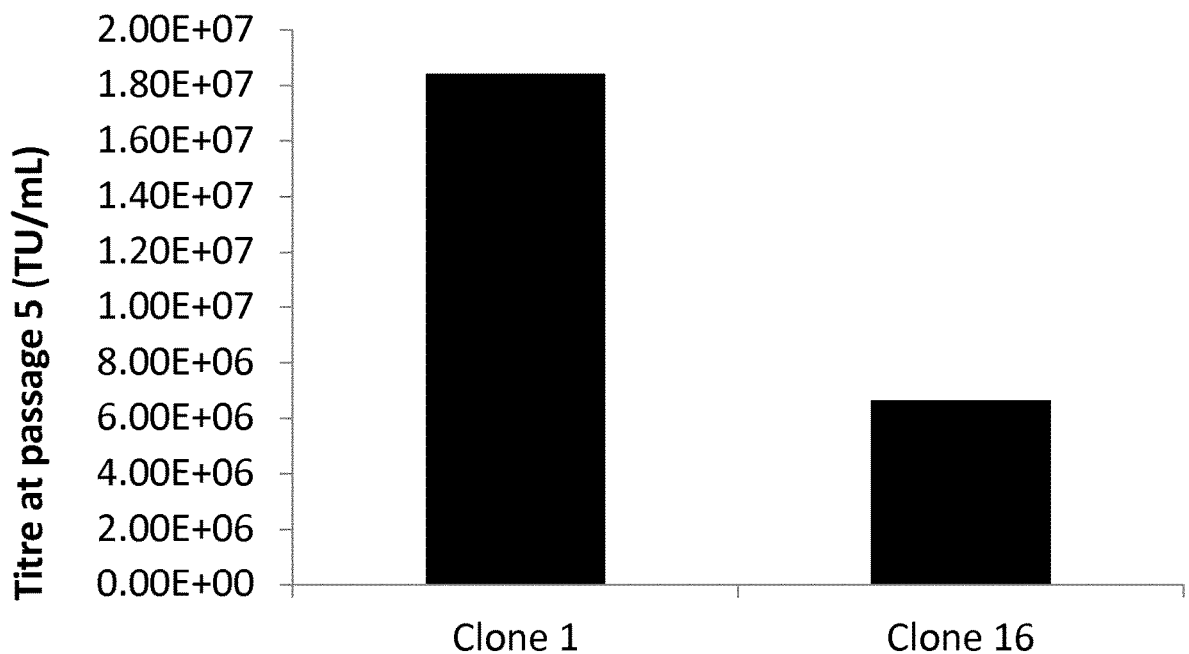
Figure 5B:
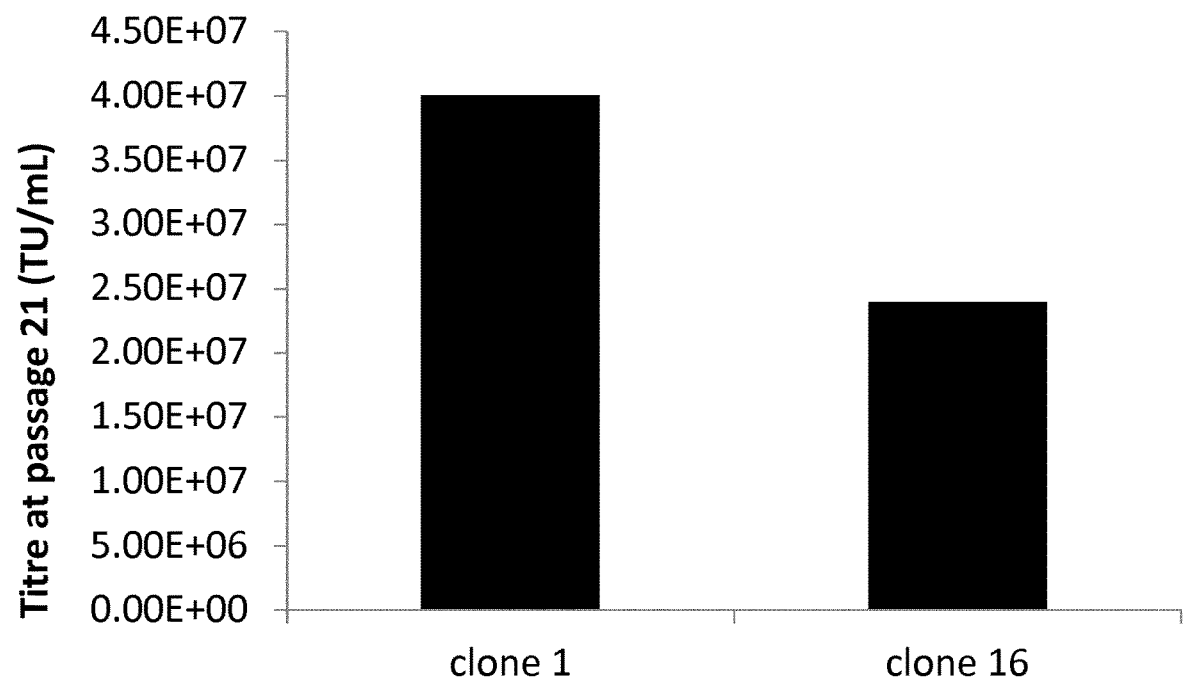

Clones 1 and 16 as described in FIG. 4 were passaged in culture and induced and titred at later timepoints to determine whether vector production was stable from these highly productive clones. As shown in FIGS. 5A and 5B, vector titres from these clones actually increased modestly between passage 5 and passage 21, possibly due to an increase in sodium butyrate concentration introduced into the induction method.

Example 6: Construct Guide (BAC+DHFR)

FIG. 6 shows a stepwise guide to the construction of BACpackWTGP-DHFR-277delU5 and BACpackSYNGP-DHFR-277delU5. Owing to the compatible ends of an XbaI and NheI digest, the lentiviral packaging genes are progressively loaded into the pSmart BAC vector. At the point of GagPol addition, 2 constructs are made containing either Wild type GagPol (WTGP) or the codon optimised GagPol, SYNGP. These are given the nomenclature of BACpack-WTGP and of BACpack-SYNGP respectively. The DHFR cassette and subsequently the transfer cassette are then loaded onto both of these constructs and so generating BACpackWTGP-DHFR-277delU5 and BACpackSYNGP-DHFR-277delU5.

Example 7: Selection of a Stable Polyclonal Pool and Genomic Amplification by MTX Solution Polyclonal stable transfectant pools are generated by transfecting the adherent cell line, HEK293T, with BACpackWTGP-DHFR-277delU5 or BACpackSYNGP-DHFR-277delU5. Successful integration events are then selected for with Zeocin, and the ability of these polyclonal pools to generate lentiviral vector are assessed after induction with Doxycycline and compared to untransfected HEK293T cells. The transfected adherent cells are transferred to a serum-free medium and grown in Erlenmeyer flasks under shaking conditions to adapt the cells to grow in suspension.

To generate lentiviral vector producing suspension cell lines, the polyclonal stable pool are adapted to grow in suspension. This is followed by genomic amplification of the retroviral genes and the transgene by subjecting the cells to increasing concentrations of MTX stepwise. The cells are seeded in media containing 100 µg/ml of MTX and grown for 14-21 days, or until the viability is greater than 90%, before being subjected to the next highest concentration of MTX. To see whether amplification of the retroviral genes has occurred, after each round of amplification, the nucleic acid vector copy number is assessed by droplet digital PCR; and the ability to generate lentiviral vectors is compared to that of the previous step.

Example 8: Construct Guide (BAC+GS)

FIG. 8 shows a stepwise guide to the construction of a LV-BAC construct containing the gs selection marker gene by replacement of the DHFR expression cassette with a GS expression cassette. A MauBI-MreI fragment is generated by overlapping PCR using the LV-BAC and pTAR-GS-RFP vectors as templates for the BAC and gs sequences, respectively, (FIGS. 3A and 3B). Owing to the blunt ends of the polymerase product, the amplicon is sub-cloned into pCR™-Blunt II-TOPO™ Vector (FIG. 3C) prior to loading into MauBI-MreI digested LV-BAC (FIG. 3D). This construct is given the nomenclature of BAC2.0_GS.

Example 9: Modification of Mammalian Cells to Knockout GS Gene

HEK293T cells are transfected with Zinc Fingers Nucleases (ZFNs) targeting the gs gene and ZFN activity in the transfected pool is confirmed and measured by CELL-I or T7 assay. Cell clones are generated from the transfected pool, and up to 500 clones are screened to identify those with frame-shifting indels (insertions or deletions) in all copies of the gs gene. Positive clones are expanded, banked, and genotype is confirmed by PCR amplification of modified sequences, followed by sequencing.

Example 10: Transfection of GS Negative HEK293T Cells and Selection of a Stable Polyclonal Pool Using MSX Up to three clones of GS knockout cells and parental HEK293T cells are transfected with a LV-BAC construct. Successful integration events are initially selected for with Zeocin, and the ability of the GS knockout HEK293T clones to generate lentiviral vector is assessed after induction with Doxycycline and compared to the transfected parental HEK293T cell line. The best lentiviral vector producer among GS negative clones is then chosen for transfection with BAC2.0_GS. After transfection, integration of the BAC into transcriptionally active regions is selected for with a single round of different MSX concentrations (0, 5, 10, 25, 50 µM) for 3-4 weeks. Zeocin is also used to select integration events of BAC2.0_GS and zeocin polyclonal pool serves as a control for the ability of the MSX stable polyclonal pools to generate lentiviral vector. Higher lentiviral productivity can be further achieved by gene amplification. The polyclonal stable pools selected with MSX are grown in media containing an increased concentration of MSX (100-500 µM) for 3-4 weeks after which the cells are expanded and lentiviral productivity is assessed. To generate lentiviral vector producing suspension cell lines, the polyclonal stable pools are adapted to grow in suspension and the stability of lentiviral production in the presence and absence of MSX is assessed.

It will be understood that the embodiments described herein may be applied to all aspects of the invention. Furthermore, all publications, including but not limited to patents and patent applications, cited in this specification are herein incorporated by reference as though fully set forth.

The invention claimed is:

1. A retroviral packaging cell comprising nucleic acid sequences encoding:
   (i) gag and pol proteins;
   (ii) env protein or vesicular stomatitis virus glycoprotein (VSVg); and
   (iii) an amplifiable selection marker;
   wherein each of the nucleic acid sequences (i), (ii) and (iii) is present as individual expression constructs, wherein said expression constructs are all integrated together at a single locus within the retroviral packaging cell genome as a unit; and
   wherein the copy number of the unit is two or more.

2. The retroviral packaging cell of claim 1, wherein the amplifiable selection marker is dihydrofolate reductase (DHFR) or glutamine synthetase (GS).

3. The retroviral packaging cell of claim 2, when the amplifiable selection marker is DHFR, wherein the expression construct comprising the nucleic acid sequence encoding DHFR comprises the nucleic acid sequence of SEQ ID NO: 1.

4. The retroviral packaging cell of claim 1, wherein the unit further comprises an expression construct comprising a nucleic acid sequence encoding a selectable marker.

5. The retroviral packaging cell of claim 1, wherein the unit further comprises an expression construct comprising a nucleic acid sequence encoding an auxiliary gene rev.

6. The retroviral packaging cell of claim 5, wherein the nucleic acid sequences encoding the gag and pol proteins, the env protein or vesicular stomatitis virus glycoprotein (VSVg), or the nucleic acid sequence of an auxiliary gene rev are derived from a retrovirus selected from lentivirus, alpha-retrovirus, gamma-retrovirus or foamy-retrovirus.

7. The retroviral packaging cell of claim 1, wherein one or more of the expression constructs comprises a CMV promoter.

8. The retroviral packaging cell of claim 1, which additionally comprises an insulator.

9. The retroviral packaging cell of claim 1, wherein the cell is a mammalian cell.

10. The retroviral packaging cell of claim 1, wherein the unit further comprises an expression construct comprising a nucleic acid sequence which encodes an RNA genome of a retroviral vector particle.

11. A retroviral producer cell comprising nucleic acid sequences encoding:
   (i) gag and pol proteins;
   (ii) env protein or vesicular stomatitis virus glycoprotein (VSVg);
   (iii) an amplifiable selection marker; and
   (iv) an RNA genome of a retroviral vector particle;
   wherein each of nucleic acid sequences (i), (ii), (iii), and (iv) is present as individual expression constructs, wherein said expression constructs are all integrated together at a single locus within the retroviral producer cell genome as a unit; and
   wherein the copy number of the unit is two or more.

12. A nucleic acid vector comprising a non-mammalian origin of replication and the ability to hold at least 25 kilobases (kb) of DNA, characterized in that said nucleic acid vector comprises nucleic acid sequences encoding:
   (i) gag and pol proteins,
   (ii) an env protein or vesicular stomatitis virus glycoprotein (VSVg), and
   (iii) an amplifiable selection marker;
   wherein each of the nucleic acid sequences (i), (ii), and (iii) is arranged as individual expression constructs within the nucleic acid vector, and wherein the nucleic acid vector further comprises one or a plurality of recombination sites.

13. The nucleic acid vector of claim 12, wherein the amplifiable selection marker is dihydrofolate reductase (DHFR) or glutamine synthetase (GS).

14. The nucleic acid vector of claim 13, when the amplifiable selection marker is DHFR, wherein the expression construct comprising the nucleic acid sequence encoding DHFR comprises the nucleic acid sequence of SEQ ID NO: 1.

15. The nucleic acid vector of claim 12, further comprising an expression construct comprising a nucleic acid sequence encoding a selectable marker.

16. The nucleic acid vector of claim 12, further comprising an expression construct comprising a nucleic acid sequence of an auxiliary gene rev.

17. The nucleic acid vector of claim 12, wherein the nucleic acid vector is selected from: a bacterial artificial chromosome, a yeast artificial chromosome, a P1-derived artificial chromosome, a fosmid or a cosmid.

18. The nucleic acid vector of claim 12, which additionally comprises nucleic acid sequences encoding an RNA genome of a retroviral vector particle.

19. A method of producing a stable retroviral packaging cell line, comprising the steps of:

(a) transfecting the nucleic acid vector of claim 12 into a culture of mammalian host cells;
(b) growing the transfected mammalian host cells in a medium which contains a concentration of a selection agent that inhibits the growth of the transfected mammalian cells which express insufficient levels of the amplifiable selection marker; and
(c) selecting transfected mammalian host cells capable of growth in said medium, wherein the selected transfected mammalian host cells contain an amplified number of copies of the nucleic acid vector integrated into the transfected mammalian host cell genome.

20. A method of producing a stable retroviral producer cell line, comprising the steps of:
(a) transfecting the nucleic acid vector of claim 18 into a culture of mammalian host cells;
(b) growing the transfected mammalian host cells in a medium which contains a concentration of a selection agent that inhibits the growth of the transfected mammalian host cells which express insufficient levels of the amplifiable selection marker; and
(c) selecting transfected mammalian host cells capable of growth in said medium, wherein the selected transfected mammalian host cells contain an amplified number of copies of the nucleic acid vector integrated into the transfected mammalian host cell genome.

21. The method of claim 19, wherein steps (b) and (c) are repeated two or more times.

22. The method of claim 19, further comprising a step, after step (a), of selecting within the culture for a mammalian host cell which has the nucleic acid sequences encoded on the vector integrated into the mammalian host cell genome.

23. The method of claim 19, wherein the selection agent is a DHFR inhibitor or a GS inhibitor.

24. A retroviral packaging cell obtained by the method of claim 19.

25. A retroviral producer cell obtained by the method of claim 20.

26. A method of producing a replication defective retroviral vector particle, comprising the steps of:
(a) transfecting the nucleic acid vector of claim 12 into a culture of mammalian host cells;
(b) growing the transfected mammalian host cells in a medium which contains a concentration of a selection agent that inhibits the growth of the transfected mammalian host cells which express insufficient levels of the amplifiable selection marker;
(c) selecting transfected mammalian host cells capable of growth in said medium, wherein the selected transfected mammalian host cells contain an amplified number of copies of the nucleic acid vector integrated into the transfected mammalian host cell genome; and
(d) further culturing the mammalian host cells selected in step (c) under conditions in which the replication defective retroviral vector particle is produced.

27. The method of claim 26, additionally comprising the step of isolating the replication defective retroviral vector particle.

28. The retroviral packaging cell of claim 9, wherein the mammalian cell is HEK 293T.

29. The nucleic acid vector of claim 17, wherein the nucleic acid vector is a bacterial artificial chromosome.

* * * * *

SEQUENCE LISTING

<160> NUMBER OF SEQ ID NOS: 1

<210> SEQ ID NO 1
<211> LENGTH: 2621
<212> TYPE: DNA
<213> ORGANISM: Artificial sequence
<220> FEATURE:
<223> OTHER INFORMATION: construct comprising dhfr gene

<400> SEQUENCE: 1

| | | | | | |
|---|---|---|---|---|---|
| cagctgtgga | atgtgtgtca | gttagggtgt | ggaaagtccc | caggctcccc agcaggcaga | 60 |
| agtatgcaaa | gcatgcatct | caattagtca | gcaaccaggt | gtggaaagtc cccaggctcc | 120 |
| ccagcaggca | gaagtatgca | aagcatgcat | ctcaattagt | cagcaaccat agtcccgccc | 180 |
| ctaactccgc | ccatcccgcc | cctaactccg | cccagttccg | cccattctcc gccccatggc | 240 |
| tgactaattt | tttttattta | tgcagaggcc | gaggccgcct | cggcctctga gctattccag | 300 |
| aagtagtgag | gaggcttttt | tggaggccta | ggcttttgca | aaaagctttc ttggatagct | 360 |
| tgggggggg | acagctcagg | gctgcgattt | cgcgccaaac | ttgacggcaa tcctagcgtg | 420 |
| aaggctggta | ggattttatc | cccgctgcca | tcatggttcg | accattgaac tgcatcgtcg | 480 |
| ccgtgtccca | agatatgggg | attggcaaga | acggagacct | accctggcct ccgctcagga | 540 |
| acgagttcaa | gtacttccaa | agaatgacca | acctcttc | agtggaaggt aaacagaatc | 600 |
| tggtgattat | gggtaggaaa | acctggttct | ccattcctga | agaatcga cctttaaagg | 660 |
| acagaattaa | tatagttctc | agtagagaac | tcaaagaacc | accacgagga gctcattttc | 720 |
| ttgccaaaag | tttggatgat | gccttaagac | ttattgaaca | accggaattg gcaagtaaag | 780 |
| tagacatggt | ttggatagtc | ggaggcagtt | ctgtttacca | ggaagccatg aatcaaccag | 840 |
| gccacctcag | actctttgtg | acaaggatca | tgcaggaatt | tgaaagtgac acgttttttcc | 900 |
| cagaaattga | tttggggaaa | tataaacttc | tcccagaata | cccaggcgtc ctctctgagg | 960 |
| tccaggagga | aaaaggcatc | aagtataagt | ttgaagtcta | cgagaagaaa gactaagatc | 1020 |
| tttgtgaagg | aaccttactt | ctgtggtgtg | acataattgg | acaaactacc tacagagatt | 1080 |
| taaagctcta | aggtaaatat | aaaatttttta | agtgtataat | gtgttaaact actgattcta | 1140 |
| attgtttgtg | tattttagat | tccaacctat | ggaactgatg | aatgggagca gtggtggaat | 1200 |
| gcctttaatg | aggaaaacct | gttttgctca | gaagaaatgc | catctagtga tgatgaggct | 1260 |
| actgctgact | ctcaacattc | tactcctcca | aaaaagaaga | gaaaggtaga agaccccaag | 1320 |
| gactttcctt | cagaattgct | aagttttttg | agtcatgctg | tgtttagtaa tagaactctt | 1380 |
| gcttgctttg | ctatttacac | cacaaaggaa | aaagctgcac | tgctatacaa gaaaattatg | 1440 |
| gaaaaatatt | ctgtaacctt | tataagtagg | cataacagtt | ataatcataa catactgttt | 1500 |
| tttcttactc | cacacaggca | tagagtgtct | gctattaata | actatgctca aaaattgtgt | 1560 |
| acctttagct | ttttaatttg | taaggggtt | aataaggaat | atttgatgta tagtgccttg | 1620 |
| actagagatc | ataatcagcc | ataccacatt | tgtagaggtt | ttacttgctt taaaaaacct | 1680 |
| cccacacctc | cccctgaacc | tgaaacataa | aatgaatgca | attgttgttg ttaacttgtt | 1740 |
| tattgcagct | tataatggtt | acaaataaag | caatagcatc | acaaatttca caataaagc | 1800 |
| attttttttca | ctgcattcta | gttgtggttt | gtccaaactc | atcaatgtat cttatcatgt | 1860 |
| ctggatcccc | aggaagctcc | tctgtgtcct | cataaaccct | aacctcctct acttgagagg | 1920 |
| acattccaat | cataggctgc | ccatccaccc | tctgtgtcct | cctgttaatt aggtcactta | 1980 |
| acaaaaagga | aattgggtag | gggttttca | cagaccgctt | tctaagggta atttttaaaat | 2040 |

```
atctgggaag tcccttccac tgctgtgttc cagaagtgtt ggtaaacagc ccacaaatgt    2100
caacagcaga aacatacaag ctgtcagctt tgcacaaggg cccaacaccc tgctcatcaa    2160
gaagcactgt ggttgctgtg ttagtaatgt gcaaaacagg aggcacattt tccccacctg    2220
tgtaggttcc aaaatatcta gtgttttcat ttttacttgg atcaggaacc cagcactcca    2280
ctggataagc attatcctta tccaaaacag ccttgtggtc agtgttcatc tgctgactgt    2340
caactgtagc attttttggg gttacagttt gagcaggata tttggtcctg tagtttgcta    2400
acacaccctg cagctccaaa ggttccccac caacagcaaa aaaatgaaaa tttgacccct    2460
gaatgggttt tccagcacca tttttcatgag ttttttgtgt ccctgaatgc aagtttaaca    2520
tagcagttac cccaataacc tcagttttaa cagtaacagc ttcccacatc aaaatatttc    2580
cacaggttaa gtcctcattt aaattaggca aaggaattct t                        2621
```